US011207115B2

(12) United States Patent
Schumacher et al.

(10) Patent No.: US 11,207,115 B2
(45) Date of Patent: Dec. 28, 2021

(54) SYSTEM AND METHOD OF COUPLING AN ALIGNMENT GUIDE TO AN INTRAMEDULLARY NAIL INSERTION HANDLE

(71) Applicant: DEPUY SYNTHES PRODUCTS, INC., Raynham, MA (US)

(72) Inventors: Yvonne Schumacher, Solothurn (CH); Gaser El Zoghbi, Solothurn (CH); This Aebi, Grenchen (CH); John V. Hunt, Cincinnati, OH (US)

(73) Assignee: DePuy Synthes Products, LLC, Raynham, MA (US)

( * ) Notice: Subject to any disclaimer, the term of this patent is extended or adjusted under 35 U.S.C. 154(b) by 218 days.

(21) Appl. No.: 16/690,543

(22) Filed: Nov. 21, 2019

(65) Prior Publication Data

US 2021/0153919 A1     May 27, 2021

(51) Int. Cl.
| | |
|---|---|
| *A61B 17/92* | (2006.01) |
| *A61B 17/17* | (2006.01) |
| *A61B 17/16* | (2006.01) |
| *A61B 17/72* | (2006.01) |
| *A61B 17/74* | (2006.01) |
| *A61B 17/86* | (2006.01) |
| *A61B 17/00* | (2006.01) |
| *A61B 17/90* | (2006.01) |

(52) U.S. Cl.
CPC .......... *A61B 17/921* (2013.01); *A61B 17/164* (2013.01); *A61B 17/7233* (2013.01); *A61B 17/744* (2013.01); *A61B 17/864* (2013.01); *A61B 17/90* (2021.08); *A61B 2017/00477* (2013.01)

(58) Field of Classification Search
CPC ... A61B 17/921; A61B 17/7233; A61B 17/90; A61B 17/1717; A61B 17/1725
See application file for complete search history.

(56) References Cited

U.S. PATENT DOCUMENTS

| | | | |
|---|---|---|---|
| 5,207,682 | A | 5/1993 | Cripe |
| 5,704,941 | A | 1/1998 | Jacober et al. |
| 6,258,095 | B1 | 7/2001 | Lombardo et al. |
| 7,131,974 | B2 | 11/2006 | Keyer et al. |
| 7,357,804 | B2 | 4/2008 | Binder, Jr. et al. |

(Continued)

OTHER PUBLICATIONS

Stryker T2 Tibial Nailing System Operative Technique, Content ID: T2-ST-3 Rev1, 32 Pages.

*Primary Examiner* — Christian A Sevilla
(74) *Attorney, Agent, or Firm* — Wayne C. Jaeschke, Jr.

(57) ABSTRACT

In one example, a system has an insertion handle that can be coupled to an intramedullary nail and includes a first coupler that defines one of a recess and a projection, and one of a latch and an abutment surface. The system has an aiming guide that includes a guide body that defines at least one alignment aperture therethrough. The aiming guide includes a second coupler that can couple the guide body to the first coupler such that the at least one alignment aperture is positioned to guide an instrument towards at least one bone-anchor fixation hole of the intramedullary nail. The second coupler defines another of the recess and the projection, and another of the latch and the abutment surface. The first and second couplers can couple to one another by receiving the projection in the recess and by engaging the latch with the abutment surface.

12 Claims, 14 Drawing Sheets

(56) References Cited

U.S. PATENT DOCUMENTS

| | | | |
|---|---|---|---|
| 7,618,420 B2 | 11/2009 | Collazo | |
| 9,308,004 B2 | 4/2016 | Giersch et al. | |
| 2002/0151897 A1* | 10/2002 | Zirkle, Jr. | A61B 17/72 606/62 |
| 2006/0253120 A1* | 11/2006 | Anderson | A61B 17/808 606/86 R |
| 2008/0264109 A1* | 10/2008 | Ritchey | A61B 17/8897 66/88 |
| 2009/0112209 A1* | 4/2009 | Parrott | A61B 17/1717 606/62 |
| 2009/0299375 A1* | 12/2009 | Wack | A61B 17/921 606/96 |
| 2013/0172890 A1* | 7/2013 | Limouze | A61B 17/921 606/62 |
| 2014/0094821 A1 | 4/2014 | Wagner et al. | |
| 2014/0214045 A1* | 7/2014 | Felder | A61B 17/921 606/104 |
| 2018/0078294 A1* | 3/2018 | Hedgeland | A61B 17/725 |

\* cited by examiner

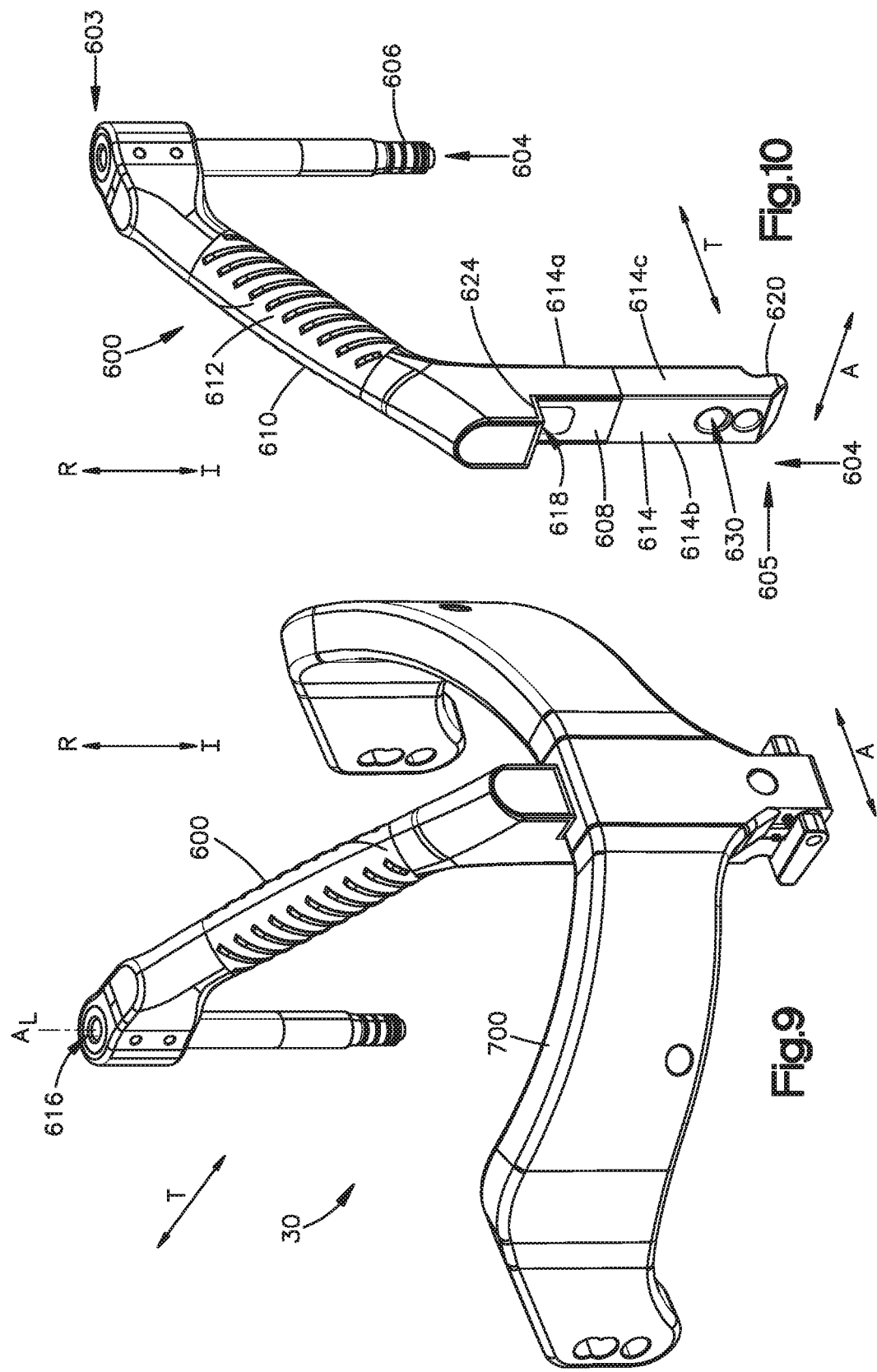

SYSTEM AND METHOD OF COUPLING AN ALIGNMENT GUIDE TO AN INTRAMEDULLARY NAIL INSERTION HANDLE

TECHNICAL FIELD

The present disclosure relates to systems, assemblies, and methods for the insertion and fixation of a nail into an intramedullary canal of a bone.

BACKGROUND

Intramedullary nails are commonly used to treat fractures in long bones of the body such as fractures in femurs, tibias, and humeri. To treat such fractures, the intramedullary nail is inserted into a medullary canal of the long bone such that the nail spans across one or more fractures to fragments of the long bone that are separated by the one or more fractures. Bone anchors are then inserted through the bone and into the intramedullary nail at opposing sides of the fracture, thereby fixing the intramedullary nail to the bone. The intramedullary nail can remain in the medullary canal at least until the fracture is fused.

SUMMARY

In an example, a system comprises an insertion handle and an aiming arm. The insertion handle is configured to couple to an intramedullary nail. The insertion handle includes a first coupler that defines one of a recess and a corresponding projection, and one of a latch and a corresponding latch abutment surface. The system comprises an aiming guide that includes a guide body that defines at least one alignment aperture therethrough. The aiming guide includes a second coupler configured to couple the guide body to the first coupler of the insertion handle such that the at least one alignment aperture is positioned to guide an instrument towards at least one bone-anchor fixation hole of the intramedullary nail when the insertion handle is coupled to the intramedullary nail. The second coupler defines another of the recess and the corresponding projection, and another of the latch and the corresponding latch abutment surface. The first and second couplers are configured to be coupled to one another by receiving the corresponding projection in the recess and engaging the latch with the corresponding latch abutment surface.

In another example, a system, comprises an insertion handle, and aiming guide, and a latch. The insertion handle is configured to couple to an intramedullary nail such that the intramedullary nail extends along a longitudinal direction. The aiming guide includes a guide body that defines at least one alignment aperture therethrough. The aiming guide is configured to be supported by the insertion handle such that, when the insertion handle is coupled to the intramedullary nail, the aiming guide is offset from the intramedullary nail along a transverse direction and the at least one alignment aperture is positioned to guide an instrument towards at least one bone-anchor fixation hole of the intramedullary nail. The latch is pivotally coupled to a body of one of the insertion handle and the aiming guide. The latch is configured to pivot about a pivot axis that extends along a lateral direction so as to move between a disengaged position, wherein the latch does not secure the insertion handle and the aiming guide to one another, and an engaged position, wherein the latch engages a corresponding latch abutment surface of the other one of the insertion handle and the aiming guide so as to secure the insertion handle and the aiming guide to one another.

In yet another example, a method comprises a step of moving an aiming guide and an insertion handle of an intramedullary nail towards one another so as to receive a projection of one of the aiming guide and the insertion handle into a recess of the other one of the aiming guide and the insertion handle. The method comprises a step of actuating a latch of one of the aiming guide and the insertion handle so as to cause the latch to engage a latch engagement surface of the other one of the aiming guide and the insertion handle and thereby secure the aiming guide and the insertion handle to one another such that, when the insertion handle is coupled to the intramedullary nail, at least one alignment aperture of the aiming guide is positioned to guide an instrument towards at least one bone-anchor fixation hole of the intramedullary nail.

BRIEF DESCRIPTION OF THE DRAWINGS

The following description of the illustrative examples may be better understood when read in conjunction with the appended drawings. It is understood that potential examples of the disclosed systems and methods are not limited to those depicted.

FIG. 9 shows a perspective view of an intramedullary nail insertion system according to yet another example;

FIG. 10 shows a perspective view of an insertion handle of the intramedullary nail insertion system of FIG. 9;

DETAILED DESCRIPTION OF ILLUSTRATIVE EXAMPLES

Figure 1:
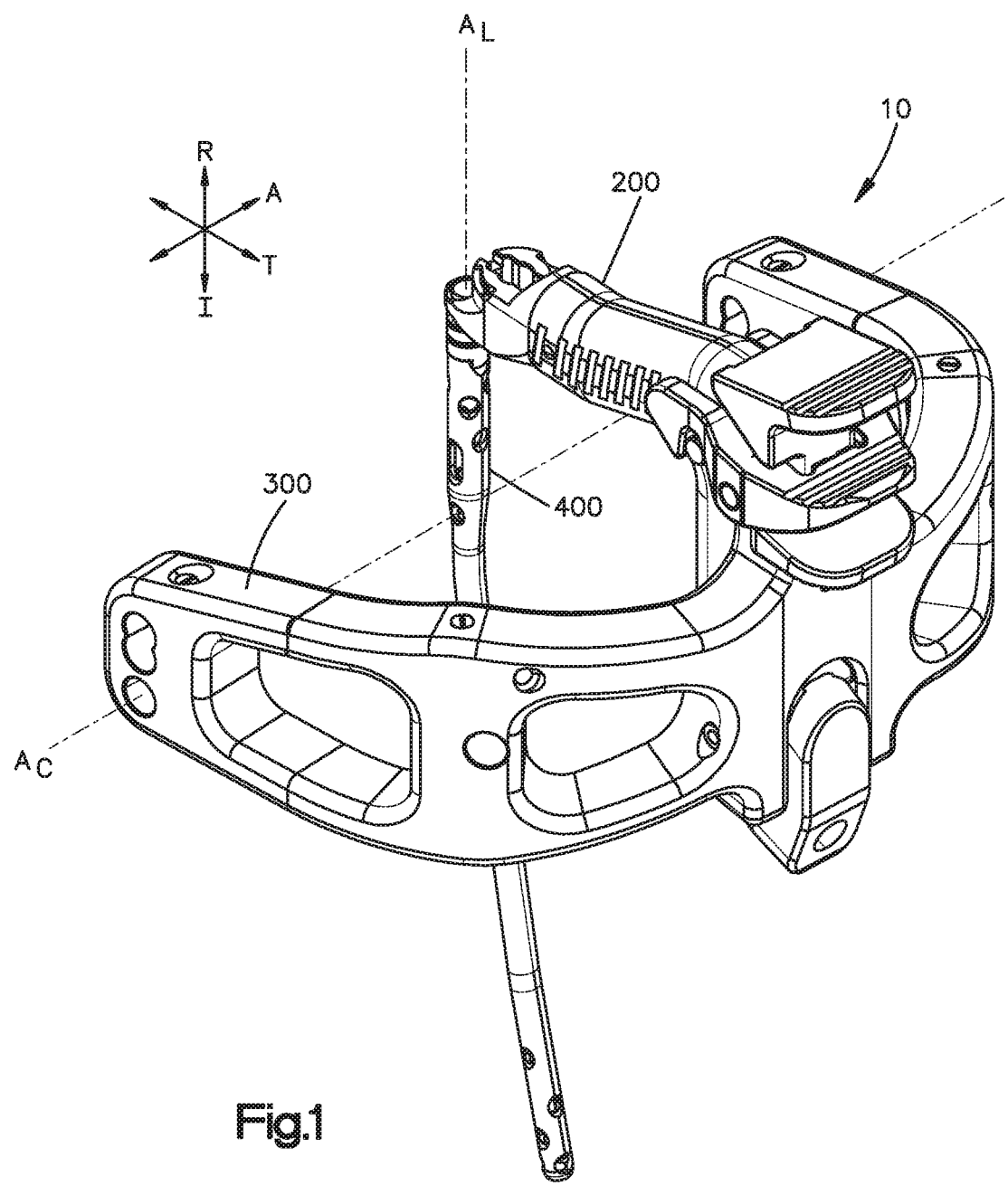
FIG. 1 shows a perspective view of an intramedullary nail insertion system according to one example.

Commonly, an intramedullary nail is implanted by driving the nail into a medullary canal of a long bone such as a tibia, fibula, humerus, or femur. Prior to insertion of the nail, the medial professional can enlarge the medullary canal to make room for the nail. For example, the medullary canal can be enlarged by inserting a reaming rod down the medullary canal, and guiding a reamer head with at least one cutting edge down the reaming rod such that the at least one cutting edge bores out the medullary canal. The reaming rod can be flexible so as to bend with the contour of the medullary canal. After enlarging the medullary canal, the intramedullary nail is then driven down into the enlarged medullary canal. In so doing, a handle can be attached to the nail, and a medical professional such as a surgeon can hold the handle to guide the intramedullary nail into the medullary canal. In some cases, the reamer head can be removed, leaving the reaming rod in place, and the intramedullary nail can then be guided down the reaming rod into the medullary canal. As such, the reaming rod can be received in a cannulation of the intramedullary nail as the nail is driven down the reaming rod into the medullary canal.

To secure the intramedullary nail to the bone, the intramedullary nail can define at least one bone-anchor fixation hole that extends at least partially through the intramedullary nail. For example, the intramedullary nail can include at least one proximal bone-anchor fixation hole at a proximal portion of the intramedullary nail and at least one distal bone-anchor fixation hole at a distal portion of the intramedullary nail. The intramedullary nail can be secured to the bone by (1) drilling, for each bone-anchor fixation hole, a hole in the bone that aligns with the bone-anchor fixation hole, and (2) inserting, for each bone-anchor fixation hole, a bone anchor through the bone and into the bone-anchor fixation hole such that the bone anchor engages the bone on at least one side, such as opposed sides, of the intramedullary nail.

This procedure, however, can present several difficulties. For example, the proximal and distal bone-anchor fixation holes are not visible to the surgeon since the intramedullary nail is disposed inside the bone. Moreover, as the intramedullary nail is driven into the medullary canal, the intramedullary nail can bend by an undetermined amount. This bending can make it difficult to predict with accuracy the location and orientation of the bone-anchor fixation holes. Therefore, a targeting system or systems can be employed to determine the location of each bone-anchor fixation hole, and/or align a cutting instrument such as a drill bit with each bone-anchor fixation hole. Once the location of a bone-anchor fixation hole is determined and/or the cutting instrument is aligned with the bone-anchor fixation hole, a hole can be drilled into the bone to the bone-anchor fixation hole. A bone anchor can subsequently be inserted through the bone and into the bone-anchor fixation hole.

One method of targeting the at least one bone-anchor fixation hole includes using fluoroscopy to obtain moving X-ray images of the position of the drill bit relative to the bone-anchor fixation hole in real-time. However, the use of fluoroscopy can over expose the patient, and particularly the surgeon who performs numerous such procedures, to harmful X-rays. As an alternative to fluoroscopy, an aiming guide can be coupled to the intramedullary nail, and the aiming guide can be used to target at least one of the bone-anchor fixation holes with a cutting instrument such as a drill bit. Generally, the aiming guide can include an alignment aperture that aligns with at least one bone-anchor fixation hole when the guide is affixed to the intramedullary nail. The cutting instrument can then be guided into the alignment aperture and through the bone to the bone-anchor fixation hole.

Coupling the aiming guide to the intramedullary nail can be cumbersome, often requiring more than two hands. Discussed herein are attachment mechanisms that are less cumbersome, more intuitive, less assembly time. In at least some examples, the aiming guide can be coupled to the intramedullary nail insertion handle using only two hands, one to hold the intramedullary nail or insertion handle, and another to hold the aiming guide. It will be understood, however, that examples herein are not limited to two-handed operations.

Referring generally to the figures, various examples of the disclosure relate to a system (e.g., 10, 20, 30, 40, 50) that comprises an insertion handle (e.g., 200, 600, 800, 1000) and an aiming guide (e.g., 300, 700, 900, 1100), and methods of using the same. The insertion handle (e.g., 200, 600, 800, 1000) is configured to quickly couple to, and quickly decouple from, the aiming guide (e.g., 300, 700, 900, 1100). The insertion handle (e.g., 200, 600, 800, 1000) is also configured to couple to an intramedullary nail (e.g., 400). In some examples, the system (e.g., 10, 20, 30, 40, 50) can comprise the intramedullary nail (e.g., 400). It will be understood, however, that the aiming guide (e.g., 300, 700, 900, 1100), the insertion handle (e.g., 200, 600, 800, 1000), and the intramedullary nail (e.g., 400) can be distributed separately from one another or can be distributed in groups of two or more of the aiming guide (e.g., 300, 700, 900, 1100), the insertion handle (e.g., 200, 600, 800, 1000), and the intramedullary nail (e.g., 400). Therefore, examples of the present disclosure can include as few as one of the aiming guide (e.g., 300, 700, 900, 1100), the insertion handle (e.g., 200, 600, 800, 1000), and the intramedullary nail (e.g., 400), or more than one, up to all, of the aiming guide (e.g., 300, 700, 900, 1100), the insertion handle (e.g., 200, 600, 800, 1000), and the intramedullary nail (e.g., 400).

In some examples, the insertion handle (e.g., 200, 600, 800, 1000) includes a coupler (208, 608, 808, 1008) that defines one of a recess (e.g., 218, 618, 818, 1018) and a corresponding projection (e.g., 316, 716, 916, 1116), and one of a latch (e.g., 314, 714, 914, 1114) and a corresponding latch abutment surface (e.g., 220, 620, 820, 1020). The aiming guide (e.g., 300, 700, 900, 1100) includes a guide body (e.g., 302, 702, 902, 1102) that defines at least one alignment aperture (e.g., 306, 706, 906, 1106) therethrough. The aiming guide (e.g., 300, 700, 900, 1100) includes another coupler (e.g., 304, 704, 904, 1104) configured to couple the guide body (e.g., 302, 702, 902, 1102) to the coupler (e.g., 208, 608, 808, 1008) of the insertion handle (e.g., 200, 600, 800, 1000) such that the at least one alignment aperture (e.g., 306, 706, 906, 1106) is positioned to guide an instrument (not shown), such as a drill bit or reamer, towards at least one bone-anchor fixation hole (e.g., 422) of the intramedullary nail when the insertion handle (e.g., 200, 600, 800, 1000) is coupled to the intramedullary nail (e.g., 400). The other coupler (e.g., 304, 704, 904, 1104) defines another of the recess (e.g., 218, 618, 818, 1018) and the corresponding projection (e.g., 316, 716, 916, 1116), and another of the latch (e.g., 314, 714, 914, 1114) and the corresponding latch abutment surface (e.g., 220, 620, 820, 1020). The coupler (e.g., 208, 608, 808, 1008) and the other coupler (e.g., 304, 704, 904, 1104) are configured to be coupled to one another by receiving the corresponding projection (e.g., 316, 716, 916, 1116) in the recess (e.g., 218, 618, 818, 1018) and by engaging the latch (e.g., 314, 714, 914, 1114) with the corresponding latch abutment surface (e.g., 220, 620, 820, 1020).

In some examples, the system (e.g., 10, 20, 30, 40, 50) comprises an insertion handle (e.g., 200, 600, 800, 1000), an aiming guide (e.g., 300, 700, 900, 1100), and a latch (e.g., 314, 714, 914, 1114). The insertion handle (e.g., 200, 600, 800, 1000) is configured to couple to an intramedullary nail (e.g., 400) such that the intramedullary nail (e.g., 400) extends along a longitudinal direction L. The aiming guide (e.g., 300, 700, 900, 1100) includes a guide body (e.g., 302, 702, 902, 1102) that defines at least one alignment aperture (e.g., 306, 706, 906, 1106) therethrough. The aiming guide (e.g., 300, 700, 900, 1100) is configured to be supported by the insertion handle (e.g., 200, 600, 800, 1000) such that, when the insertion handle (e.g., 200, 600, 800, 1000) is coupled to the intramedullary nail (e.g., 400), the aiming guide (e.g., 300, 700, 900, 1100) is offset from the intramedullary nail along a transverse direction T and the at least one alignment aperture (e.g., 306, 706, 906, 1106) is positioned to guide an instrument towards at least one bone-anchor fixation hole (e.g., 422) of the intramedullary nail (e.g., 400). The latch (e.g., 314, 714, 914, 1114) is pivotably coupled to a body of one of the insertion handle (e.g., 200, 600, 800, 1000) and the aiming guide (e.g., 300, 700, 900, 1100). The latch (e.g., 314, 714, 914, 1114) is configured to pivot about a pivot axis $A_P$ that extends along a lateral direction A so as to move between a disengaged position, wherein the latch (e.g., 314, 714, 914, 1114) does not secure the insertion handle (e.g., 200, 600, 800, 1000) and the aiming guide (e.g., 300, 700, 900, 1100) to one another, and an engaged position, wherein the latch (e.g., 314, 714, 914, 1114) engages a corresponding latch abutment surface (e.g., 220, 620, 820, 1020) of the other one of the insertion handle (e.g., 200, 600, 800, 1000) and the aiming guide (e.g., 300, 700, 900, 1100) so as to secure the insertion handle (e.g., 200, 600, 800, 1000) and the aiming guide (e.g., 300, 700, 900, 1100) to one another.

Figures 2, 3:
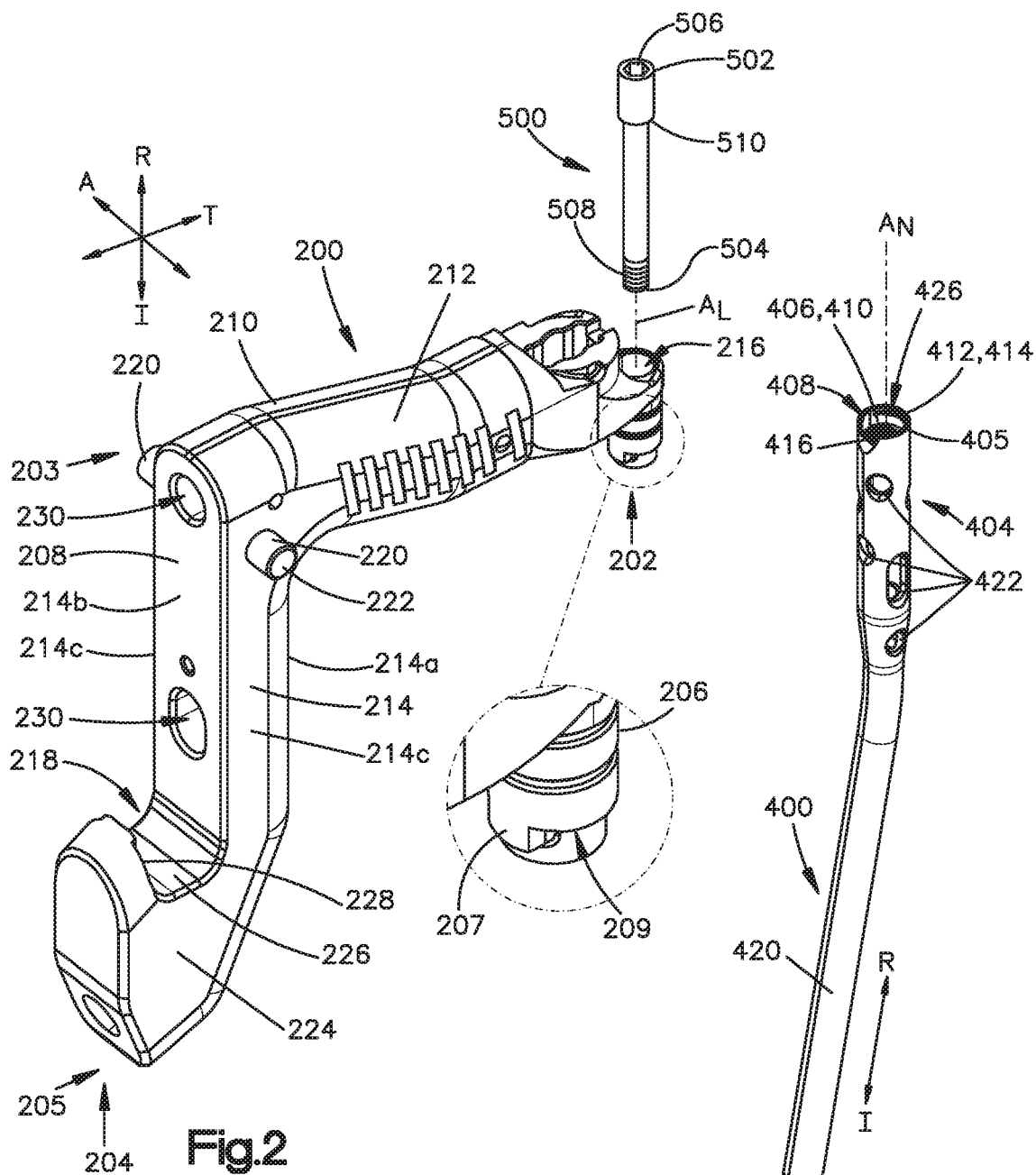
FIG. 2 shows a perspective view of an insertion handle of the intramedullary nail insertion system of FIG. 1.
FIG. 3 shows a perspective view of an intramedullary nail according to one example.

Turning more specifically to FIGS. 1 to 7, an example system 10 is shown having an aiming guide 300 (FIGS. 4 and 5) with a coupler 304. The coupler 304 defines a projection 316 and a latch 314. The system 10 also has an insertion handle 200 (FIG. 2) with a coupler 208. The coupler 208 defines a recess 218 that receives the projection 316, and a latch abutment surface 220 that engages the latch 314. As shown in FIGS. 2 and 3, the insertion handle 200 has a first transverse end 202 and a second transverse end 204 that are offset from one another along a transverse direction T. The select transverse direction T can be a radial direction that extends radially out relative to an axis of the intramedullary nail 400 when the insertion handle 200 is coupled to the intramedullary nail 400. The insertion handle 200 can have a trailing end 203, and a leading end 205 that is offset from the trailing end 203 along an insertion direction I. Stated differently, the leading end 205 can be offset from the trailing end 203 along a rearward direction R. The insertion direction I and rearward direction R can be unidirectional, and can extend along a bi-directional longitudinal direction L. The transverse direction T can be perpendicular to the longitudinal direction L.

The first transverse end 202 of the insertion handle 200 comprises a coupler 206 that is configured to couple to the intramedullary nail 400. When coupled to one another, the intramedullary nail 400 can extend along the longitudinal direction L. The coupler 206 can be configured to couple to the intramedullary nail 400 so as to fix a rotational orientation of the coupler 206 relative to the intramedullary nail 400 about an axis $A_L$. In some examples, the coupler 206 can have a cylindrical shape that extends along the axis $A_L$ along an insertion direction I. The axis $A_L$ can be a central axis of the coupler 206 and can be aligned with a central axis $A_N$ of the intramedullary nail 400 when the intramedullary nail 400 is coupled to the coupler 206. The coupler 206 can define at least one mating feature, such as at least one projection 207, at least one recess 209, or at least one projection 207 and at least one recess 209. The coupler 206 is configured to engage a corresponding at least one mating feature of the intramedullary nail 400, such as at least one protrusion 414, at least one recess 416, or at least one protrusion 414 and at least one recess 416, so as to fix a rotational orientation of the insertion handle 200 relative to the intramedullary nail 400. The at least one mating feature can be disposed at a leading end of the coupler 206. In some examples, the coupler 206 can include a plurality of mating features, such as a plurality of projections 207, each configured to engage a corresponding recess 416 of the intramedullary nail 400. In at least some such examples, adjacent ones of the projections 207 can be separated a recess 209.

When the insertion handle 200 is coupled to the intramedullary nail 400, the at least one mating feature of the insertion handle 200 engages the at least one mating feature of the intramedullary nail 400 so as to prevent the intramedullary nail 400 from rotating relative to the insertion handle 200. Moreover, in some examples, the at least one mating feature of the coupler 206 can be configured such that the insertion handle 200 can be coupled to the intramedullary nail 400 in only one select rotational orientation. Thus, the at least one mating feature of the coupler 206 can be configured so as to prevent the insertion handle 200 from being coupled to the intramedullary nail 400 in any other rotational orientation other than the select rotational orientation.

The insertion handle 200 can define a cannulation 216 that extends through the first transverse end 202 of the insertion handle 200 along the insertion direction I. The insertion handle 200 can be configured (e.g., sized and shaped) such that the cannulation 216 aligns with a cannulation 426 of the intramedullary nail 400 when the insertion handle 200 is coupled to the intramedullary nail 400. The cannulation 216 can be configured (e.g., sized and shaped) so as to receive a rod, such as a guide rod or reaming rod, therethrough. The cannulation 216 can extend through the coupler 206.

In one example, the system can comprise a fastener 500 that is configured to fasten the insertion handle 200 to the intramedullary nail 400 so as to positionally fix the insertion handle 200 and intramedullary nail 400 to one another. The fastener 500 can be configured as any suitable fastener, and various such fasteners are known in the art. FIG. 2 shows one example fastener 500 that has a first end 502, and a second end 504 offset from the first end 502 along the insertion direction I. The fastener 500 can include a shaft that extends between the first and second ends 502 and 504, and that is sized and shaped to be received through the cannulation 216 of the coupler 206 of the insertion handle 200. The second end 504 can include threading 508 that is configured to engage threading 410 of the intramedullary nail 400 so as to secure the fastener 500 to the intramedullary nail 400, although it will be understood that the second coupler end 504 can include a quick connect/disconnect or other suitable feature other than threading. In one example, the threading 508 can be male threading that is configured to engage female threading 410 of the intramedullary nail 400.

The first end 502 can include an engagement surface 506 that is configured to be engaged by an instrument or a medical professional so as to rotate the fastener 500 to engage the threading 508 of the fastener 500 with the threading 410 of the intramedullary nail 400. In one example, the engagement surface 506 can be an internal surface that defines a non-circular cross-section, such as a hexagon, polygon, or other shape, that can be engaged by a driving instrument such that rotation of the driving instrument causes a corresponding rotation of the fastener 500. In other examples, the engagement surface 506 can be an external surface or handgrip that can be gripped by a tool or a user's hand to secure the fastener 500 to the intramedullary nail 400.

The fastener 500 can include a stop or a shoulder 510 that is configured to abut the insertion handle 200 when the fastener 500 is secured to the intramedullary nail 400 so as to prevent the insertion handle 200 from moving in a rearward direction R, opposite the insertion direction I, relative to the intramedullary nail 400. The stop or shoulder 510 has a cross-sectional dimension in a plane that is perpendicular to the insertion direction I. The cross-sectional dimension can be measured from a first point on the stop or shoulder to a second point on the stop or shoulder, the first and second points being on opposed sides of the axis $A_L$. Further, the cross-sectional dimension of the stop or shoulder 510 can be greater than a cross-sectional dimension of the cannulation 216 such that the insertion handle 200 limits an insertion depth of the fastener 500 into the cannulation 216 along the insertion direction I. Thus, when the insertion handle 200 is coupled to the intramedullary nail 400, the insertion handle 200 can be trapped between the intramedullary nail 400 and the stop or shoulder 510 of the fastener 500.

Referring briefly to FIG. 3, an intramedullary nail 400 is shown according to one example. It will be understood that intramedullary nail 400 is but one example, and that other intramedullary nails can be used with the system described herein. The intramedullary nail 400 has an insertion or leading end 402, and a trailing end 404 offset from the leading end 402 along the rearward direction R, opposite the insertion direction I. The leading and trailing ends 402 and 404 can be spaced from one another along a central nail axis $A_N$ that can be straight or bent. Further, the intramedullary nail 400 has an outer surface 420 that extends between the leading and trailing ends 402 and 404, such as from the leading end 402 to the trailing end 404. In some examples, the intramedullary nail 400 can define a cannulation 426 that extends therein between the leading and trailing ends 402 and 404. The trailing end 404 can include a fastener 406 that is configured to receive the fastener 500. For example, the fastener 406 can define a recess or opening 408 that is configured to receive the fastener end 504. The fastener 406 can include female threading 410 that engages male threading 508 of the fastener 500, although other fastening mechanisms are contemplated.

The trailing end 404 can also include a fastener 412 that is configured to engage the coupler 206 of the insertion handle 200 so as to rotatably fix the insertion handle 200 and intramedullary nail 400 relative to one another with respect to rotation about the central nail axis $A_N$. In one example, the fastener 412 can comprise at least one of a protrusion 414 and a recess 416 that is configured to engage a corresponding one of a recess and a protrusion of the insertion handle 200. For example, the fastener 412 can comprise at least one protrusion 414, such a plurality of protrusions or teeth. Each protrusion 414 can be configured to engage at least one corresponding recess 209 in the insertion handle 200. Each of the at least one protrusion 414 can extend from a trailing end surface 405 of the intramedullary nail 400 towards the leading end 402 of the nail 400. The fastener 414 can define at least one recess 416, such as a plurality of recesses, that extends into the trailing end surface 405 towards the leading end 402. Each of the at least one recess 416 can be configured to receive a corresponding protrusion 207 of the insertion handle 200. Further, in examples having a plurality of protrusions 414, each of the at least one recess 416 can extend between adjacent ones of the protrusions 414. Thus, in such examples, the protrusions 414 and recesses 416 can alternate around the opening 408.

The intramedullary nail further defines a set of one or more trailing bone-anchor fixation holes 422 that extend through the outer surface 420 at the trailing end 404, and a set of one or more leading bone-anchor fixation holes 424 that extend through the outer surface 420 at the leading end 402. The set of one or more trailing apertures 422 are configured to be disposed on a first side of a fracture in a bone that defines the medullary canal, and the set of one or more leading apertures 424 are configured to be disposed on a second side of the fracture in the bone. Thus, the nail 400 can be configured such that the fracture is to be disposed between the set of one or more trailing apertures 422 and the set of one or more leading apertures 424. Each trailing aperture 422 and each leading aperture 424 is configured to receive a bone anchor such that the bone anchor fixedly attaches the intramedullary nail 400 to the bone. Each bone-anchor fixation hole 422 and 424 can be either locking aperture having threads that are configured to be engaged by threads of bone screws, or can be non-locking apertures.

Referring back to FIG. 2, the insertion handle 200 can include a gripping portion 210 that extends between the first transverse end 202 and the second transverse end 204 of the insertion handle 200. The gripping portion 210 can be between the coupler 206 and the coupler 208. The gripping portion 210 can include an outer surface 212 that extends between the first and second transverse ends 202 and 204. For example, the outer surface 212 can extend along the transverse direction T. The outer surface 212 can be sized and shaped to be gripped by a hand of a medical professional. Thus, the insertion handle 200 can be used to guide the intramedullary nail 400 along the guide rod or reaming rod into the medullary canal of the bone during insertion of the intramedullary nail 400, although it will be understood that the intramedullary nail 400 can be inserted without the guide rod or reaming rod.

The second transverse end 204 of the insertion handle 200 comprises a coupler 208 that is configured to couple the insertion handle 200 to the aiming guide 300. The coupler 208 includes at least one latch abutment surface 220 that is configured to be engaged by a latch 314 (FIG. 5) of the aiming guide 300 so as to couple the insertion handle 200 and aiming guide 300 to one another at a first location. The coupler 208 further defines a recess 218 that is configured to receive the projection 316 (FIG. 5) of the aiming guide 300 so as to couple the insertion handle 200 and aiming guide 300 to one another at a second location. The first and second locations can be offset from one another along the longitudinal direction L. For example, in FIGS. 1 to 7, the second location is offset from the first location along the insertion direction I. Thus, the recess 218 can be offset from the latch abutment surface 220 with respect to the insertion direction I.

The coupler 208 can have a coupler body 214 that extends from the gripping portion 210 along the insertion direction I. The coupler body 214 can have an inner end 214a and an outer end 214b that are offset from one another along the transverse direction T. The coupler body 214 can have opposed sides 214c that are offset from one another along a lateral direction A. The lateral direction A can be angularly offset from the longitudinal direction L and transverse direction T. In one example, the lateral direction A can be perpendicular to the longitudinal direction L and transverse direction T. The opposed sides 214c can extend between the inner and outer ends 214a and 214b. The latch abutment surface 220 can extend away from a side 214c of the body portion 214. For instance, the latch abutment surface 220 can extend along the lateral direction A. In one example, the coupler 208 can include the latch abutment surface 220 and a second latch abutment surface 220 that extend away from respective ones of the opposing sides 214c of the coupler body 214. The coupler 208 can include a pin 222 that defines each latch abutment surface 220. Each pin 222 can extend out from a respective one of the sides 214c of the coupler body 214. It will be understood that the latch abutment surface 220 can alternatively be defined between the opposed sides 214c of the coupler body 214 or by a structure other than a pin.

The coupler 208 can include a hook portion 224 that extends from the coupler body 214 along the transverse direction T. For example, the hook portion 224 can extend along the transverse direction T, away from the first transverse end 202 of the insertion handle 200. The recess 218 can extend into the hook portion 224 along the insertion direction I. The recess 218 can terminate before the leading end 205 of the insertion handle 200. In one example, the recess 218 can have a "U" shape, wherein the arms of the "U" shape are offset from one another along the transverse direction T. The recess 218 can be defined by the outer end 214b of the coupler body 214, a bottom surface 226 that extends away from the coupler body 214, and an inner surface 228 that extends from the bottom surface 220 along the rearward direction R, the inner surface 228 facing the outer end 214b of the coupler body 214. In some examples, the recess 218 can extend entirely through the insertion handle 200 along the lateral direction A. When the projection 316 of the aiming guide 300 is received in the recess 218, the inner surface 228 of the hook portion 224 and the outer end 214b of the coupler body 214 can provide an interference with the projection 316 that prevents the projection 316 from translating along the transverse direction T with respect to the insertion handle 200. When the projection 316 is received in the recess 218, the projection 316, and hence the aiming arm 300, can pivot within the recess 218 about an axis that extends along the lateral direction A.

The outer end 214b of the coupler body 214 can define an outer surface that is configured to face a corresponding surface 318 (FIG. 5) of the aiming guide 300 when the insertion handle 200 and aiming guide 300 are coupled to one another. In at least some examples, the outer surface of the coupler body 214 is configured to abut the corresponding surface 318 of the aiming guide 300. The coupler 208 can define at least one alignment recess 230 that extends into the outer end 214b of the coupler body 214. For example, the coupler 208 can define a pair of alignment recesses 230 that extend into the outer end 214b of the coupler body 214. Each alignment recess 230 can be configured to receive a corresponding alignment pin 332 (shown in FIG. 5) of the aiming guide 300. It will be understood that, in alternative examples, one or both of the recesses 230 can alternatively be implemented as a pin that is received in a corresponding alignment recess of the aiming guide 300.

Figure 4:
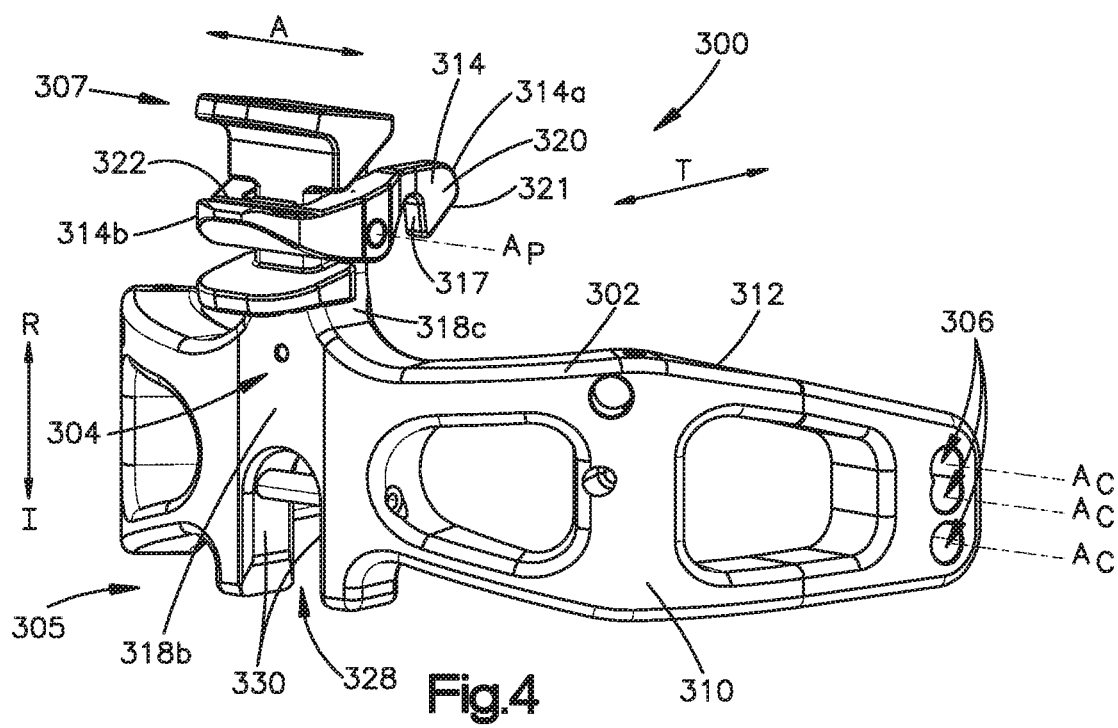
FIG. 4 shows a perspective view of an aiming guide of the intramedullary nail insertion system of FIG. 1.
Figure 5:
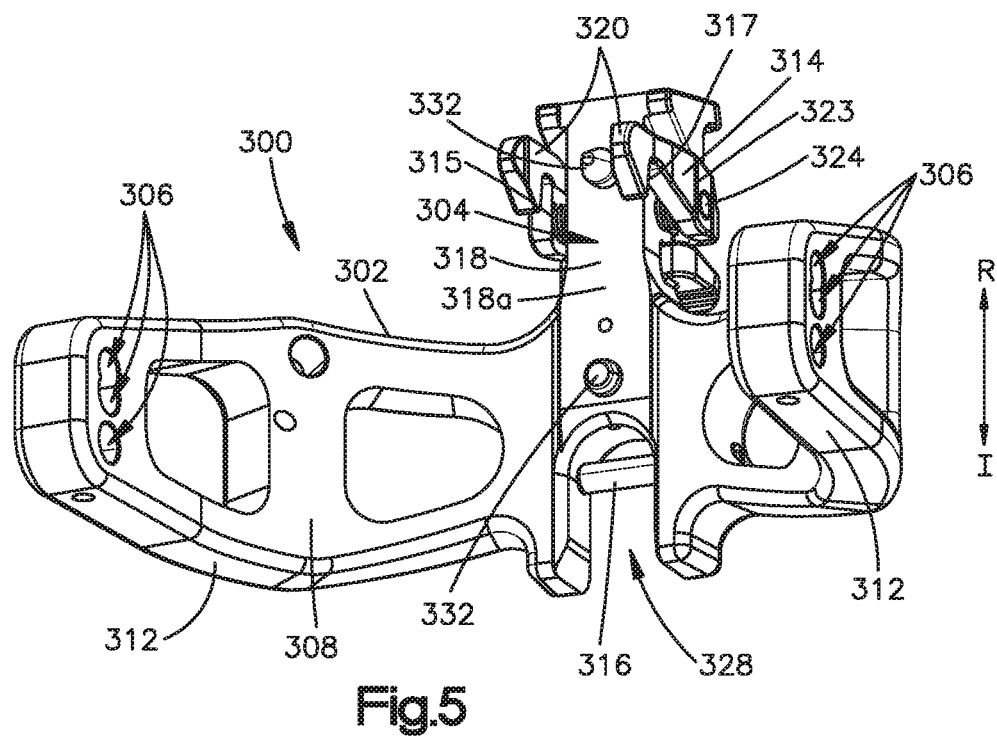
FIG. 5 shows another perspective view of the aiming guide of the intramedullary nail insertion system of FIG. 1.

With reference to FIGS. 4 and 5, the aiming guide 300 comprises a guide body 302 and a coupler 304. The guide body 302 defines at least one alignment aperture 306 therethrough. The coupler 304 is configured to couple the aiming guide 300 to the insertion handle 200 such that the at least one alignment aperture 306 is positioned to guide an instrument, such as a drill or reamer bit, towards at least one bone-anchor fixation hole 422 of the intramedullary nail 400 when the insertion handle 200 is coupled to the intramedullary nail 400.

The aiming guide 300 has an inner guide surface 308, and an outer guide surface 310 that is opposite the inner surface 308. The inner guide surface 308 can be positioned closer to the intramedullary nail 400 than the outer guide surface 310 when the aiming guide 300 is coupled to the intramedullary nail 400. The aiming guide 300 has a leading end 305 and a trailing end 307. The leading end 305 can be spaced from the trailing end 307 along the insertion direction I. Each alignment aperture 306 can extend entirely through the guide body 302 from the inner guide surface 308 to the outer guide surface 310. The guide body 302 can include at least one aiming arm 312 that extends away from the coupler 304. For example, the guide body 302 can include a pair of aiming arms 312 that extend away from the coupler 304 in opposite directions. Each aiming arm 312 can extend partially around a central axis $A_L$ that extends along the insertion direction I. For example, each aiming arm 312 can extend in a circumferential direction that extends circumferentially about the intramedullary nail 400 when the aiming guide 300 is coupled to the intramedullary nail 400. The aiming arms 312 can have any suitable configuration.

Each aiming arm 312 can include at least one alignment aperture 306. Each alignment aperture 306 can have a central axis $A_C$ that is aligned with one of the bone-anchor fixation holes 422 of the intramedullary nail 400 when the aiming guide 300 is coupled to the intramedullary nail 400 by the insertion handle 200. In some examples, at least one alignment aperture 306 can have an axis $A_C$ that is aligned with another one of the alignment apertures 306. For example, an alignment aperture 306 defined by a first one of the aiming arms 312 can have a central axis $A_C$ that is aligned with an alignment aperture 306 defined by a second one of the aiming arms 312.

The coupler 304 includes a latch 314 that is configured to engage the at least one latch abutment surface 220 of the insertion handle 200 so as to couple the insertion handle 200 and aiming guide 300 to one another at a first location. The coupler 304 further defines a projection 316 that is configured to be received in the recess 218 of the insertion handle 200 so as to couple the insertion handle 200 and aiming guide 300 to one another at a second location. The first and second locations can be offset from one another along the longitudinal direction L. For example, in FIGS. 1 to 7, the second location is offset from the first location along the insertion direction I. Thus, the projection 316 can be offset from the latch 314 with respect to the insertion direction I. It will be understood, however, that the locations of the projection 316 and the latch 314 can be reversed in alternative examples such that the latch 314 is offset from the projection 316 with respect to the insertion direction I.

The coupler 304 can have a coupler body 318 that extends along the insertion direction I. The coupler body 318 can have an inner end 318a and an outer end 318b that are offset from one another along the transverse direction T. The coupler body 318 can have opposed sides 318c that are offset from one another along a lateral direction A. Each aiming arm 312 can extend from one of the opposed sides 318c. The opposed sides 318c can extend between the inner and outer ends 318a and 318b.

The latch 314 can be configured to pivot about a pivot axis $A_P$. The pivot axis $A_P$ can extend along the lateral direction A. Thus, the latch 314 can be configured to pivot between a disengaged position, wherein the latch 314 does not engage a latch abutment surface 220 of the insertion handle 200, and an engaged position wherein the latch 314 engages a latch abutment surface 220 of the insertion handle 200. The latch 314 can include a spring 315 that biases the latch 314 towards the engaged position.

The latch 314 can include at least one engagement surface 317 that is configured to engage the latch abutment surface 220 of the insertion handle 200 when the latch 314 is in the engaged position. The latch 314 can include at least one hook 320 that is configured to engage a latch abutment surface 220 of the insertion handle 200 when the latch 314 is in the engaged position. For example, the latch 314 can include a pair of hooks 320, each configured to engage a respective latch abutment surface 220 of the insertion handle 200. The pair of hooks 320 can be offset from one another along the lateral direction A. For example, the hooks 320 can be disposed on opposed sides 318c of the coupler body 318. Each hook 320 can include an inner engagement surface 317 that is configured to engage a respective latch abutment surface 220. In some examples, at least one of the hooks 320 can have a ramped surface 321, which can be configured to assist in moving the latch 314 from the engaged position to the disengaged position as discussed below. Each ramped surface 321 can be opposite an engagement surface 317.

The latch 314 can include an actuation member 322 that is configured to be depressed and released by a user, such as a medical professional, so as to move the latch 314 between the engaged position and the disengaged position. For example, the latch 314 can be configured such that, when the actuation member 322 is depressed, the at least one hook 320 moves to a disengaged configuration, and when the actuation member 322 is released, the spring 315 causes the at least one hook 320 to move to the engaged position.

The latch 314 can include a first latch end 314a and a second latch end 314b that are offset from one another along the transverse direction T. The first latch end 314a can include the at least one hook 320, and the second latch end 314b can include the actuation member 322. In some examples, the actuation member 322 can extend from the one of the hooks 320 to the other one of the hooks 320. The pivot axis $A_P$ can extend between the first and second latch ends 314a and 314b along the lateral direction A.

The latch 314 can include at least one arm 323 that is coupled to the coupler body 318. The coupler 304 can include a pivot pin 324 that couples the at least one arm 323 to the coupler body 318 such that the latch 314 pivots about the pivot pin 324. Thus, the at least one arm 323 can be pivotably coupled to the coupler body 318. In some examples, the latch 314 can include a pair of arms 323 that offset from one another along the lateral direction A. The pair of arms 323 can be coupled to opposing sides 318c of the coupler body 318. Each arm 323 can define one of the hooks 320. The pivot axis $A_P$ can extend from one of the arms 323 to the other one of the arms 323. However, it will be understood that, the latch 314 can be configured in another suitable manner in alternative examples.

In some examples, the aiming guide 300 can include a pair of opposed gripping surfaces 326 (shown in FIG. 7) that offset from one another along the insertion direction I. The gripping surfaces 326 can face away from one another. The actuation member 322 can be spaced between the gripping surfaces 326. The gripping surfaces 326 can protect the actuation member 322 from accidental actuation. Further, the gripping surfaces 326 can be gripped by a user, such as by thumb and pointer finger, so as to position the aiming arm 300 as the aiming arm 300 is coupled to the insertion handle 200. It will be understood, however, that examples of the disclosure can be devoid of the opposed gripping surfaces 326.

The projection 316 can include an outer surface that extends along the lateral direction A. The projection 316 can be a pin that has a central axis that extends along the lateral direction A. The aiming guide 300 can define a recess 328 that into the leading end 305 towards the trailing end 307. In one example, the recess 328 can have a "U" shape. The recess 328 can entirely extend through the aiming guide 300 from the inner surface 308 to the outer surface 310. The aiming guide 300 can including opposing inner surfaces 330 that are offset from one another along the lateral direction A and that define the recess 328. The projection 316 can be disposed within the recess 328. For example, the projection 316 can extend from one of the inner surfaces 330 to the other one of the inner surfaces 330. In alternative examples, the projection 316 can be configured in another suitable manner. For example, the aiming guide 300 can devoid of the recess 328, and the projection 316 can instead extend from the leading end 305 of the aiming guide 300 along the insertion direction I. As one example, see FIG. 8 discussed below.

The inner end 318a of the coupler body 318 can define an inner surface that is configured to face a corresponding outer surface of the insertion handle 200 when the insertion handle 200 and aiming guide 300 are coupled to one another. In at least some examples, the inner surface of the coupler body 318 is configured to abut the corresponding surface of the outer end 214b of the insertion handle 200. The coupler 304 can define at least one alignment pin 332 that extends from the inner end 318a of the coupler body 318. For example, the coupler 304 can include a pair of alignment pins 332 that extend from the inner end 318a of the coupler body 318. Each alignment pin 332 can be configured to be received a corresponding alignment recess 230 of the insertion handle 200. It will be understood that, in alternative examples, one or both of the alignment pins 332 can alternatively be implemented as an alignment recess that receives a corresponding alignment pin of the insertion handle 200.

Figure 6:
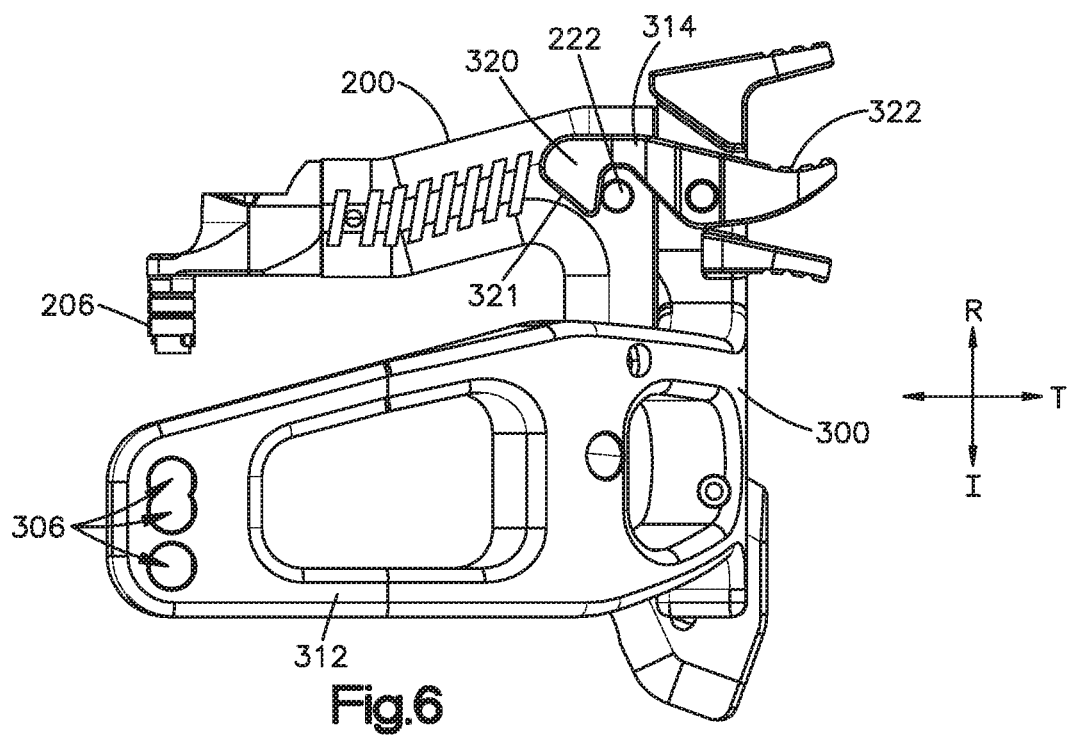
FIG. 6 shows a side view of the intramedullary nail insertion system of FIG. 1 without the intramedullary nail.
Figure 7:
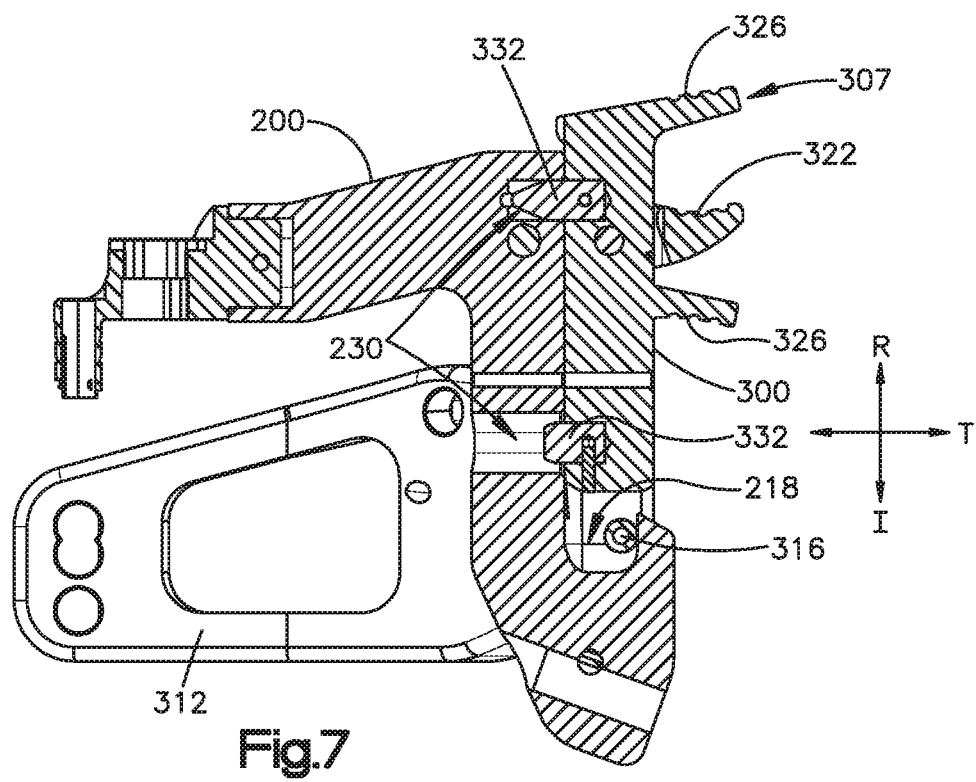
FIG. 7 shows a cross-sectional side view of the intramedullary nail insertion system of FIG. 1 without the intramedullary nail.

In operation, and with reference to FIGS. 6 and 7, the system 20 can be assembled by moving the aiming guide 300 towards the insertion handle 200 along the insertion direction I so as to receive the projection 316 of the aiming guide 300 into the recess 218 of the insertion handle 200. The recess 218 is configured such that, when the recess 218 receives the projection 316, the insertion handle 200 limits translational movement of the aiming guide 300 with respect to the insertion direction I. However, the aiming guide 300 can be pivoted or rotated relative to the insertion handle 200 about the projection 316 such that the trailing end 307 of the aiming guide 300 moves towards the insertion handle 200. As the aiming guide 300 is pivoted, each alignment pin 322 can be received in a corresponding one of the alignment recesses 230. Additionally, or alternatively, the inner end 318a of the coupler body 318 can abut the outer end 214b of the insertion handle 200.

The latch 314 can then be actuated so as to cause the latch 314 to engage the latch engagement surface 220 and thereby secure the aiming guide 300 and the insertion handle 200 to one another such that, when the insertion handle 200 is coupled to the intramedullary nail 400, at least one alignment aperture 306 of the aiming guide is positioned to guide an instrument towards at least one bone-anchor fixation hole 422 of the intramedullary nail 400. In some examples, as the aiming guide 300 is pivoted, the at least one ramped surface 321 of the latch 314 can ride along the at least one latch abutment surface 220 of the insertion handle 200 so as to cause the latch 314 to move from the engaged position to the disengaged position. When the ramped surface 321 moves past the latch abutment surface 220, the latch 314 can spring back towards the engaged position such that the at least one hook 320 engages the at least one latch abutment surface 220. In other examples, as the aiming guide 300 is pivoted, the user can depress the actuation member 322 so as to cause the latch 314 to move from the engaged position to the disengaged position. When the at least one hook 320 moves past the at least one latch abutment surface 220, the user can release the actuation member 322, thereby allowing the latch 314 to spring back towards the engaged position such that the at least one hook 320 engages the at least one latch abutment surface 220. When the at least one latch 314 engages the at least one latch abutment surface 220, the insertion handle 200 can be fixed to the aiming guide 300 with respect to translation along the insertion direction I, translation along the transverse direction T, and rotation away from the aiming guide 300. The latch 314 can provide an audible and/or tactile feedback, such as click, when the latch 314 engages the at least one latch abutment surface 220.

To decouple the aiming guide 300 from the insertion handle 200, the user can depress the actuation member 322 so as to cause the latch 314 to move from the engaged position to the disengaged position. The user can then pivot the aiming guide 300 relative to the insertion handle 200 about the projection 316 so that the trailing end 307 of the aiming guide 300 moves away from the insertion handle 200, and the user can remove the projection 316 of the aiming guide 300 from the recess 218 of the insertion handle 200 along the rearward direction R.

Figure 8:
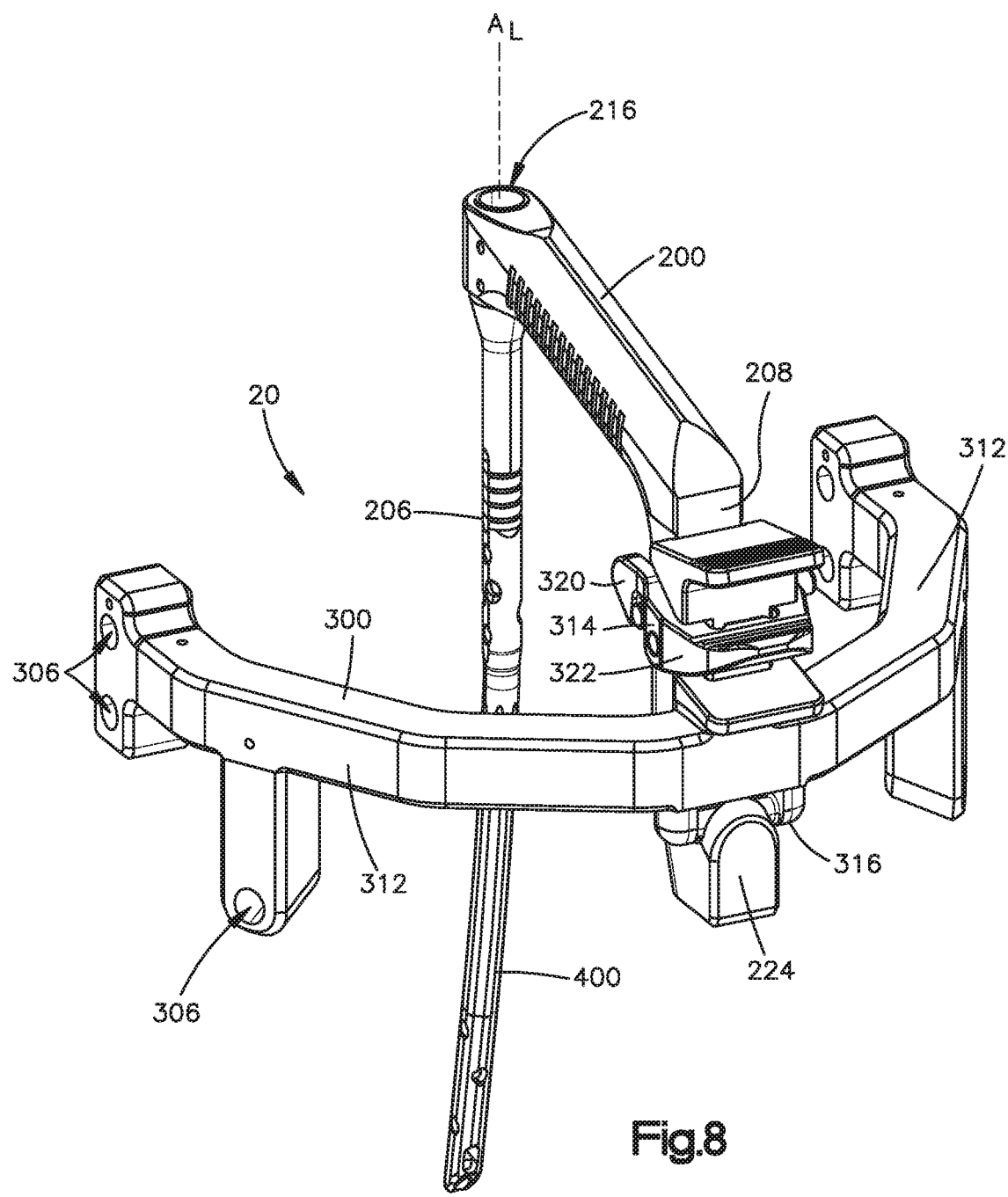
FIG. 8 shows a perspective view of an intramedullary nail insertion system according to another example.

Referring briefly to FIG. 8, an alternative example of a system 20 is shown. The system 20 has a handle 200 that is configured in a manner similar to that described above. Further, the system 20 has an aiming guide 300 that is configured in a manner similar to that described above with a few notable exceptions. First, each aiming arm 312 has an alternative shape than that shown in FIGS. 1 to 7. Second, the aiming guide 300 is devoid of a recess 328, and the projection 316 extends from the leading end 305 of the aiming guide 300.

Turning now to FIGS. 9 to 14, an example system 30 is shown having an aiming guide 700 (FIG. 12) with a coupler 704 that defines a projection 716 and a latch 714, and having an insertion handle 600 (FIG. 10) with a coupler 608 that defines a recess 618 that receives the projection 716 and a latch abutment surface 620 that engages the latch 714. As shown in FIG. 10, the insertion handle 600 has a first transverse end 602 and a second transverse end 604 that are offset from one another along the transverse direction T. The insertion handle 600 can have a trailing end 603, and a leading end 605 that is offset from the trailing end 603 along the insertion direction I.

The first transverse end 602 of the insertion handle 600 comprises a coupler 606 that is configured to couple to the intramedullary nail 400. The coupler 606 can be configured in a manner similar to that described above in relation to coupler 206 of FIGS. 1 to 7. Therefore, the description of coupler 206 above can equally apply to coupler 606. The insertion handle 600 can also define a cannulation 616 that extends through the first transverse end 602 of the insertion handle 600 along the insertion direction I. The insertion handle 600 can be configured (e.g., sized and shaped) such that the cannulation 616 aligns with a cannulation 426 of the intramedullary nail 400 when the insertion handle 600 is coupled to the intramedullary nail 400. The cannulation 616 can be configured (e.g., sized and shaped) so as to receive a rod, such as a guide rod or reaming rod, therethrough. The cannulation 616 can extend through the coupler 606. In some examples, the system 30 can comprise a fastener 500 that is configured as described above in relation to FIGS. 1 to 7 (or in another suitable manner) and that is configured to fasten the insertion handle 600 to the intramedullary nail 400 so as to positionally fix the insertion handle 600 and intramedullary nail 400 to one another.

The insertion handle 600 can include a gripping portion 610 that extends between the first transverse end 602 and the second transverse end 604 of the insertion handle 600. The gripping portion 610 can be between the coupler 606 and the coupler 608. The gripping portion 610 can include an outer surface 612 that extends between the first and second transverse ends 602 and 604. For example, the outer surface 612 can extend along the transverse direction T. The outer surface 612 can be sized and shaped to be gripped by a hand of a medical professional. Thus, the insertion handle 600 can be used to guide the intramedullary nail 400 along the guide rod or reaming rod into the medullary canal of the bone during insertion of the intramedullary nail 400, although it will be understood that the intramedullary nail 400 can be inserted without the guide rod or reaming rod.

The second transverse end 604 of the insertion handle 600 comprises a coupler 608 that is configured to couple the insertion handle 600 to the aiming guide 700. The coupler 608 includes at least one latch abutment surface 620 that is configured to be engaged by a latch 714 (shown in FIG. 11) of the aiming guide 700 so as to couple the insertion handle 600 and aiming guide 700 to one another at a first location. The coupler 608 further defines a recess 618 that is configured to receive the projection 716 (shown in FIG. 11) of the aiming guide 700 so as to couple the insertion handle 600 and aiming guide 700 to one another at a second location. The first and second locations can be offset from one another along the longitudinal direction L. For example, in FIGS. 9 to 19, the first location is offset from the second location along the insertion direction I. Thus, the latch abutment surface 620 can be offset from the recess 618 with respect to the insertion direction I.

The coupler 608 can have a coupler body 614 that extends from the gripping portion 610 along the insertion direction I. The coupler body 614 can have an inner end 614a and an outer end 614b that are offset from one another along the transverse direction T. The coupler body 614 can have opposed sides 614c that are offset from one another along a lateral direction A. The opposed sides 614c can extend between the inner and outer ends 614a and 614b. The latch abutment surface 620 can be defined at the leading end 605 of the coupler 608, such as at a terminal end of the coupler 608. In some examples, the coupler 608 can include a projection that defies the latch abutment surface 620 and extends from the coupler body 614 along the insertion direction I. In other examples, the latch abutment surface 620 can be defined at a leading end of the coupler body 614. The latch abutment surface 620 can be defined at the inner end 614a of the coupler body 614a. Thus, the latch abutment surface 620 can face the transverse direction T towards the first transverse end 602 of the insertion handle 600. The latch abutment surface 620 can extend along the lateral direction A. It will be understood that the latch abutment surface 620 can be alternatively defined.

The coupler 608 can include a shoulder 624 that extends from the coupler body 614 along the transverse direction T. For example, the shoulder 624 can extend along the transverse direction T, away from the first transverse end 602 of the insertion handle 600. The recess 618 can extend into the shoulder 624 along the insertion direction I. The recess 618 can have a closed shape in a plane that extends along the lateral direction A and the transverse direction T. When the projection 716 of the aiming guide 700 is received in the recess 618, the inner surface of the recess 618 can provide an interference with the projection 716 that prevents the projection 716 from translating along the transverse direction T with respect to the insertion handle 600. The shoulder 624 can provide an interference with the aiming guide 700 that prevents the aiming guide 700 from moving along the rearward direction R with respect to the insertion handle 600.

The outer end 614b of the coupler body 614 can define an outer surface that is configured to face a corresponding surface 718a (shown in FIG. 12) of the aiming guide 700 when the insertion handle 600 and aiming guide 700 are coupled to one another. In at least some examples, the outer surface of the coupler body 614 is configured to abut the corresponding surface 718a (shown in FIG. 12) of the aiming guide 700. The coupler 608 can define at least one alignment recess 630 that extends into the outer end 614b of the coupler body 614. Each alignment recess 630 can be configured to receive a corresponding alignment pin 732 of the aiming guide 700. It will be understood that, in alternative examples, one or both of the alignment recesses 630 can alternatively be implemented as an alignment pin that is configured to be received in a corresponding alignment recess of the aiming guide 700.

Figure 11:
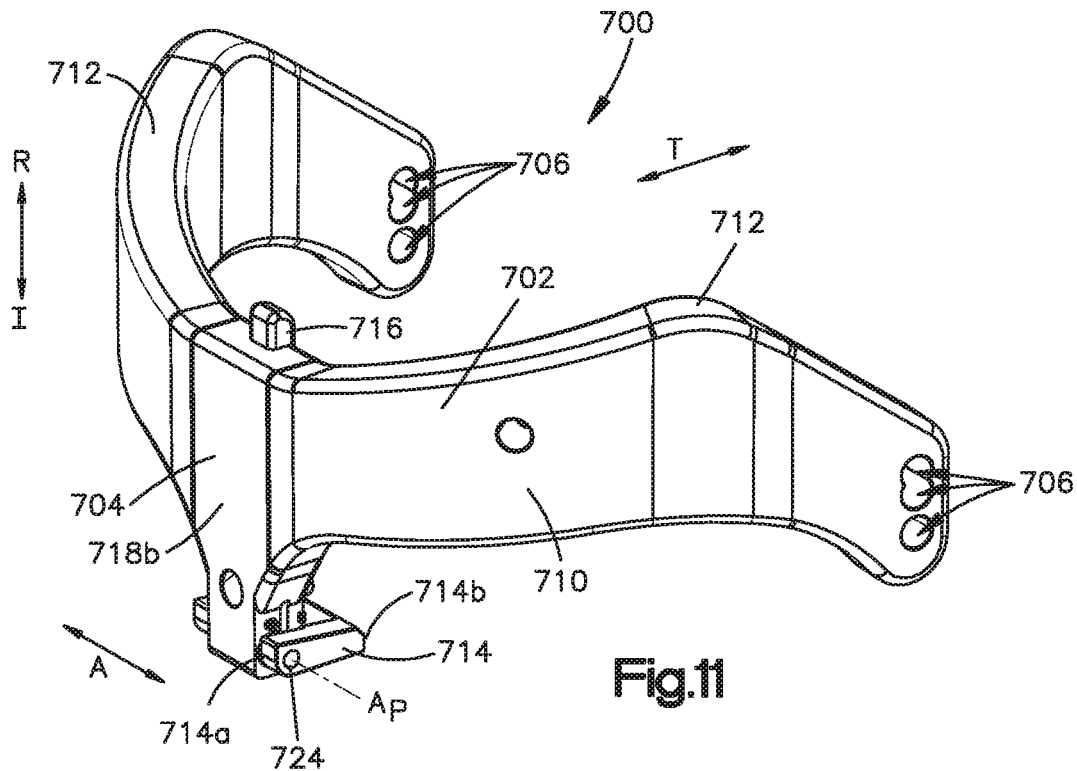
FIG. 11 shows a perspective view of an aiming guide of the intramedullary nail insertion system of FIG. 9.
Figure 12:
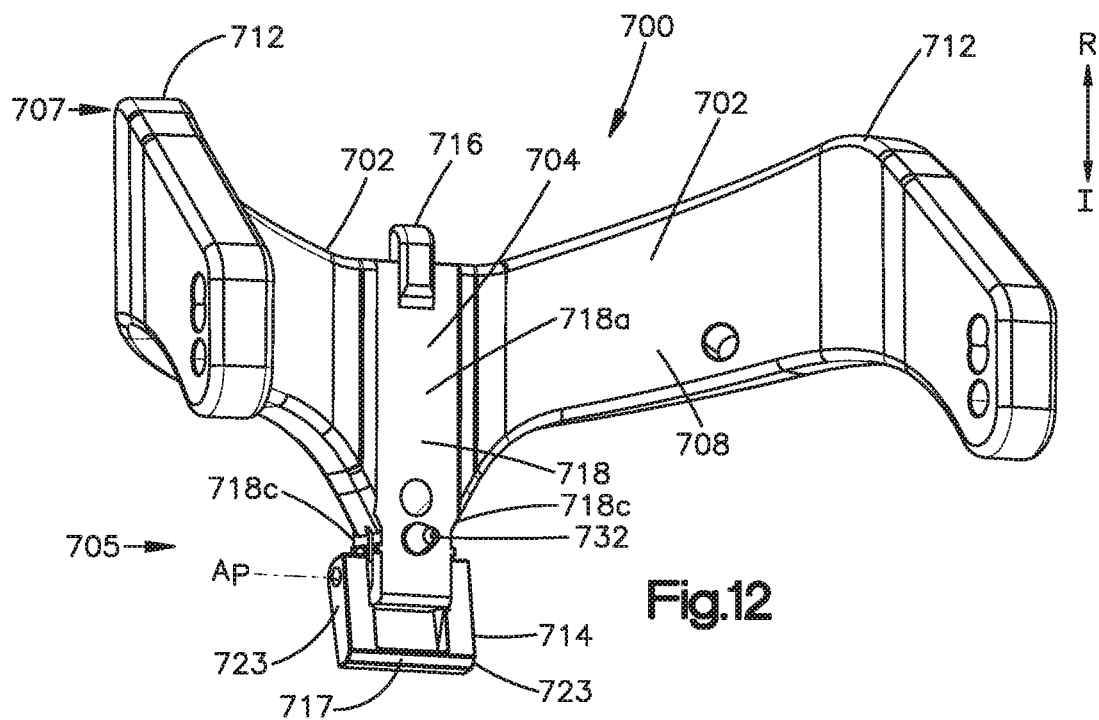
FIG. 12 shows another perspective view of the aiming guide of the intramedullary nail insertion system of FIG. 9.

With reference to FIGS. 11 and 12, the aiming guide 700 comprises a guide body 702 and a coupler 704. The guide body 702 defines at least one alignment aperture 706 therethrough. The coupler 704 is configured to couple the aiming guide 700 to the insertion handle 600 such that the at least one alignment aperture 706 is positioned to guide an instrument, such as a drill or reamer bit, towards at least one bone-anchor fixation hole 422 of the intramedullary nail 400 when the insertion handle 600 is coupled to the intramedullary nail 400.

The aiming guide 700 has an inner guide surface 708, and an outer guide surface 710 that is opposite the inner surface 708. The inner guide surface 708 can be positioned closer to the intramedullary nail 400 than the outer guide surface 710 when the aiming guide 700 is coupled to the intramedullary nail 400. The aiming guide 700 has a leading end 705 and a trailing end 707. The leading end 705 can be spaced from the trailing end 707 along the insertion direction I. Each alignment aperture 706 can extend entirely through the guide body 702 from the inner guide surface 708 to the outer guide surface 710. The guide body 702 can include at least one aiming arm 712 that extends away from the coupler 704. For example, the guide body 702 can include a pair of aiming arms 712 that extend away from the coupler 704 in opposite directions. Each aiming arm 712 can extend partially around a central axis $A_L$ (shown in FIG. 9) that extends along the insertion direction I. For example, each aiming arm 712 can extend in a circumferential direction that extends circumferentially about the intramedullary nail 400 when the aiming guide 700 is coupled to the intramedullary nail 400. The aiming arms 712 can have any suitable configuration.

Each aiming arm 712 can include at least one alignment aperture 706. Each alignment aperture 706 can have a central axis $A_C$ that is aligned with one of the bone-anchor fixation holes 422 of the intramedullary nail 400 when the aiming guide 700 is coupled to the intramedullary nail 400 by the insertion handle 600. In some examples, at least one alignment aperture 706 can have an axis $A_C$ that is aligned with another one of the alignment apertures 706. For example, an alignment aperture 706 defined by a first one of the aiming arms 712 can have a central axis $A_C$ that is aligned with an alignment aperture 706 defined by a second one of the aiming arms 712.

The coupler 704 includes a latch 714 that is configured to engage the at least one latch abutment surface 620 of the insertion handle 600 so as to couple the insertion handle 600 and aiming guide 700 to one another at a first location. The coupler 704 further defines a projection 716 that is configured to be received in the recess 618 (shown in FIG. 10) of the insertion handle 600 so as to couple the insertion handle 600 and aiming guide 700 to one another at a second location. The projection 716 can extend from the coupler 704 along the rearward direction R. The first and second locations can be offset from one another along the longitudinal direction L. For example, in FIGS. 9 to 14, the first location is offset from the second location along the insertion direction I. Thus, the latch 714 can be offset from the projection 716 with respect to the insertion direction I. It will be understood, however, that the locations of the projection 716 and the latch 714 can be reversed in alternative examples such that the projection 716 is offset from the latch 714 along the insertion direction I.

The coupler 704 can have a coupler body 718 that extends along the insertion direction I. The coupler body 718 can have an inner end 718a and an outer end 718b that are offset from one another along the transverse direction T. The coupler body 718 can have opposed sides 718c that are offset from one another along a lateral direction A. Each aiming arm 712 can extend from one of the opposed sides 718c. The opposed sides 718c can extend between the inner and outer ends 718a and 718b.

The latch 714 can be configured to pivot about a pivot axis $A_P$. The pivot axis $A_P$ can extend along the lateral direction A. Thus, the latch 714 can be configured to pivot between a disengaged position (shown in FIG. 12), wherein the latch 714 is not positioned to engage a latch abutment surface 620 of the insertion handle 600, and an engaged position (shown in FIG. 11) wherein the latch 714 is positioned to engage a latch abutment surface 620 of the insertion handle 600. The latch 714 can include a spring that biases the latch 714 towards the engaged position, although the latch 714 can be devoid of the spring in other examples.

The latch 714 can include at least one engagement surface 717 that is configured to engage the latch abutment surface 620 of the insertion handle 600 when the latch 714 is in the engaged position. The at least one engagement surface 717 can be spaced from the pivot axis $A_P$. For example, the latch 714 can define an opening 720 between the at least one engagement surface 717 and the pivot axis $A_P$. The latch 714 can be configured to pivot between the disengaged position, wherein the latch abutment surface 620 of the insertion handle 600 is not received in the opening 720, and the engaged position, wherein the latch abutment surface 620 is received in the opening 720. The opening 720 can extend along a plane. The plane can extend along the lateral direction A in at least one of the disengaged and engaged positions. The latch 714 can define a closed shape around the opening 720 in the plane, although it will be understood that the latch 714 can define an open shape in alternative examples. The opening 720 can extend at least partially, such as entirely, through the latch 714 along a direction that is perpendicular to the plane.

The latch 714 can include at least one arm 723 that is coupled to the coupler body 718. The coupler 704 can include a pivot pin 724 that couples the at least one arm 723 to the coupler body 718 such that the latch 714 pivots about the pivot pin 724. Thus, the at least one arm 723 can be pivotably coupled to the coupler body 718. In some examples, the latch 714 can include a pair of arms 723 that offset from one another along the lateral direction A. The pair of arms 723 can be coupled to opposing sides 718c of the coupler body 718. The pivot axis $A_P$ can extend from one of the arms 723 to the other one of the arms 723. In some examples, the at least one engagement surface 717 can extend between the pair of arms 723, such as from one of the arms 723 to the other one of the arms 723. The latch 714 can include a first latch end 714a and a second latch end 714b that are offset from one another. The pivot axis $A_P$ can extend between the first and second latch ends 714a and 714b along the lateral direction A. The pivot pin 724 can extend through the latch 714 adjacent to the first latch end 714a, and the at least one engagement surface 717 can be disposed adjacent to the second latch end 714b. However, it will be understood that, the latch 714 can be configured in another suitable manner in alternative examples.

The inner end 718a of the coupler body 718 can define an inner surface that is configured to face a corresponding outer surface of the insertion handle 600 when the insertion handle 600 and aiming guide 700 are coupled to one another. In at least some examples, the inner surface of the coupler body 718 is configured to abut the corresponding surface of the outer end 614b of the insertion handle 600. The coupler 704 can define at least one alignment pin 732 that extends from the inner end 718a of the coupler body 718. For example, the coupler 704 can include a pair of alignment pins 732 that extend from the inner end 718a of the coupler body 718. Each alignment pin 732 can be configured to be received a corresponding alignment recess 630 of the insertion handle 600. It will be understood that, in alternative examples, one or both of the alignment pins can alternatively be configured as an alignment recess that is configured to mate with a corresponding alignment pin of the insertion handle 600.

Figure 13:
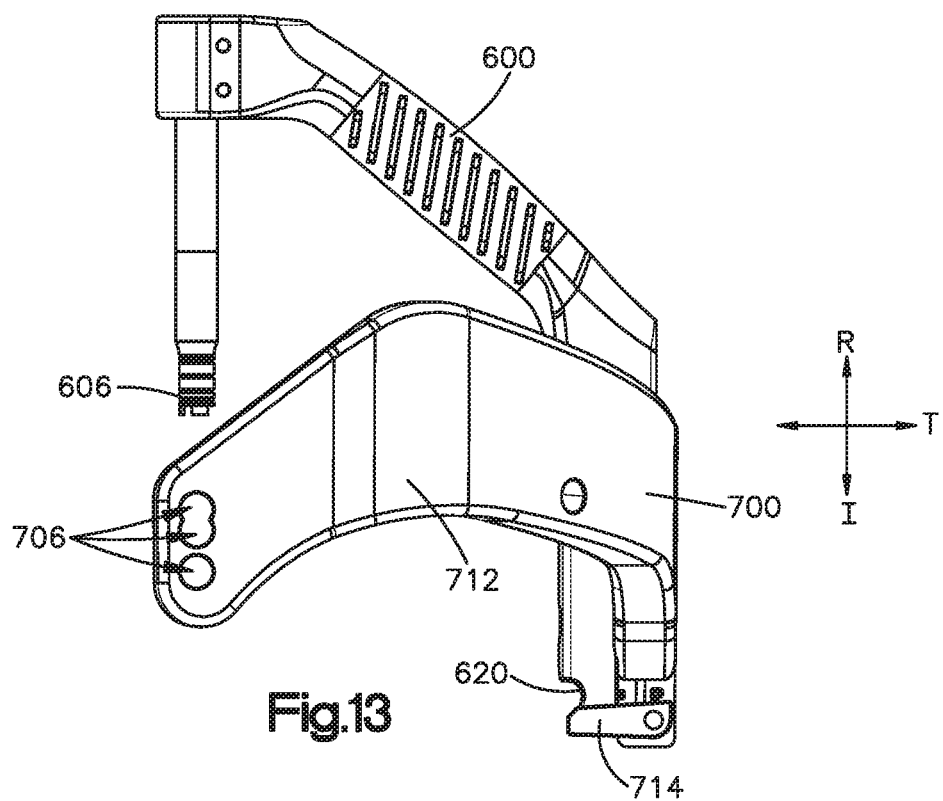
FIG. 13 shows a side view of the intramedullary nail insertion system of FIG. 9.
Figure 14:
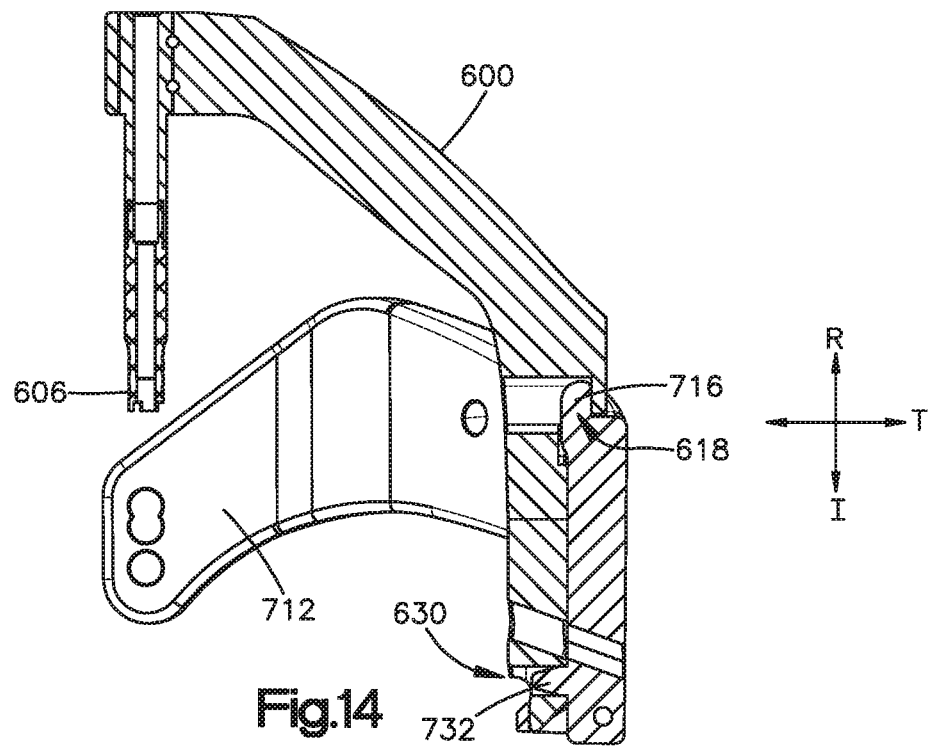
FIG. 14 shows a cross-sectional side view of the intramedullary nail insertion system of FIG. 9.
Figure 15:
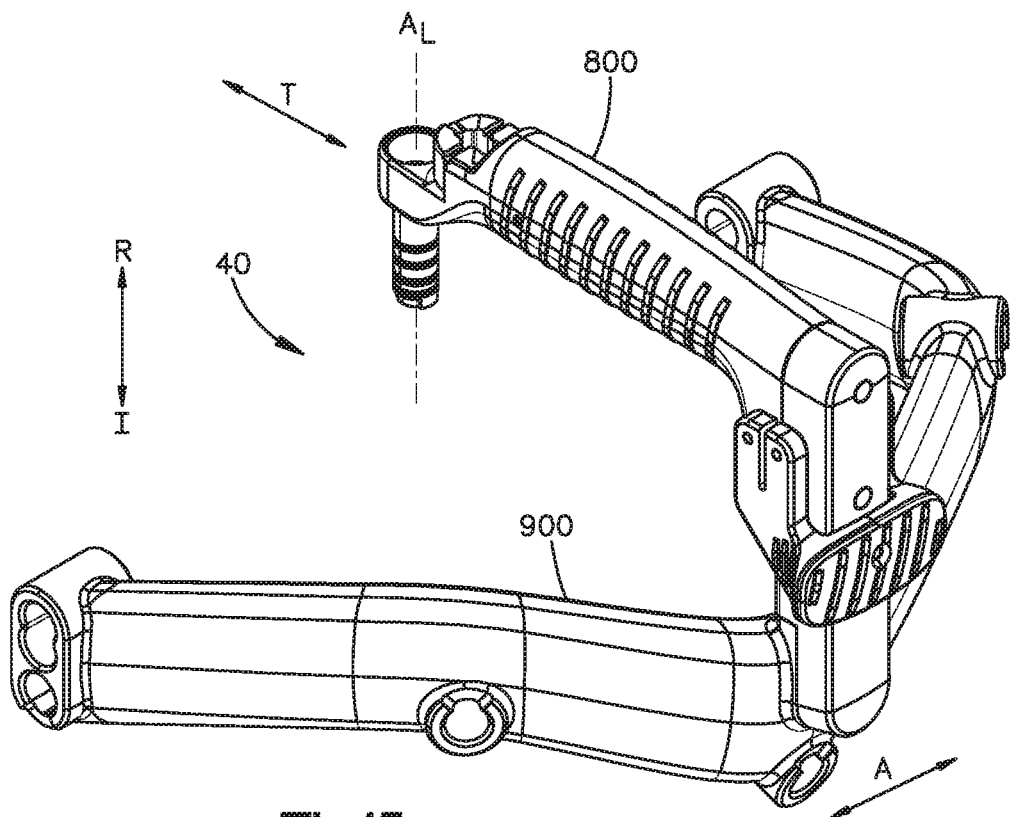
FIG. 15 shows a perspective view of an intramedullary nail insertion system according to yet still another example.

In operation, and with reference to FIGS. 13 and 14, the system 30 can be assembled by moving the aiming guide 700 towards the insertion handle 600 along the rearward direction R so as to receive the projection 716 of the aiming guide 700 into the recess 618 of the insertion handle 600. The recess 618 is configured such that, when the recess 618 receives the projection 716, the insertion handle 600 limits translational movement of the projection 716 of the aiming guide 700 with respect to the rearward direction R. However, the aiming guide 700 can be pivoted or rotated relative to the insertion handle 600 about the projection 716 such that the trailing end 707 of the aiming guide 700 moves towards the insertion handle 600. As the aiming guide 700 is pivoted, each alignment pin 732 can be received in a corresponding one of the alignment recesses 630. Additionally, or alternatively, the inner end 718a of the coupler body 718 can abut the outer end 614b of the insertion handle 600. The latch 714 can then be actuated so as to cause the latch 714 to engage the latch engagement surface 620 and thereby secure the aiming guide 700 and the insertion handle 600 to one another such that, when the insertion handle 600 is coupled to the intramedullary nail 400, at least one alignment aperture 706 of the aiming guide is positioned to guide an instrument towards at least one bone-anchor fixation hole 422 of the intramedullary nail 400. For example, the at least one latch 714 can be moved from the disengaged position to the engaged position such that the abutment surface 717 abuts the latch abutment surface 620. When the at least one latch 714 engages the at least one latch abutment surface 620, the insertion handle 600 can be fixed to the aiming guide 700 with respect to translation along the insertion direction I, translation along the transverse direction T, and rotation away from the aiming guide 700. The latch 714 can provide an audible and/or tactile feedback, such as click, when the latch 714 engages the at least one latch abutment surface 620.

To decouple the aiming guide 700 from the insertion handle 600, the user can move the latch 714 to move from the engaged position to the disengaged position. The user can then pivot the aiming guide 700 relative to the insertion handle 600 about the projection 716 so that the trailing end 707 of the aiming guide 700 moves away from the insertion handle 600, and the user removes the projection 716 of the aiming guide 700 from the recess 618 of the insertion handle 600 along the rearward direction R.

Figure 16:
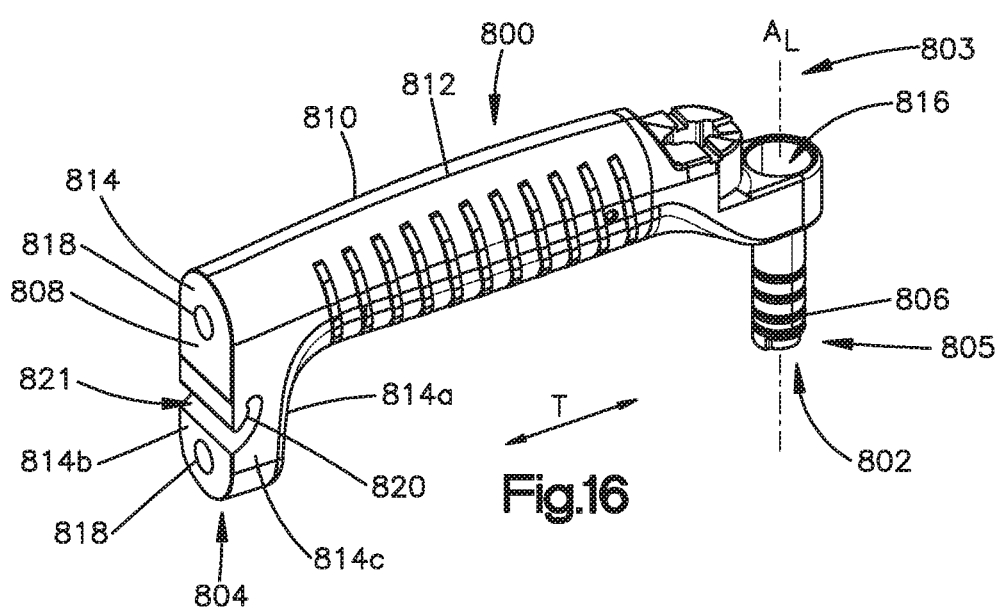
FIG. 16 shows a perspective view of an insertion handle of the intramedullary nail insertion system of FIG. 15.

Turning now to FIGS. 15 to 20, an example system 40 is shown having an aiming guide 900 (FIG. 18) with a coupler 904 that defines a projection 916 and a latch 914, and having an insertion handle 800 (FIG. 16) with a coupler 808 that defines a recess 818 that receives the projection 916 and a latch abutment surface 820 that engages the latch 914. As shown in FIG. 16, the insertion handle 800 has a first transverse end 802 and a second transverse end 804 that are offset from one another along the transverse direction T. The insertion handle 800 can have a trailing end 803, and a leading end 805 that is offset from the trailing end 803 along the insertion direction I.

The first transverse end 802 of the insertion handle 800 comprises a coupler 806 that is configured to couple to the intramedullary nail 400. The coupler 806 can be configured in a manner similar to that described above in relation to coupler 806 of FIGS. 1 to 7. Therefore, the description of coupler 206 above can equally apply to coupler 806. The insertion handle 800 can also define a cannulation 816 that extends through the first transverse end 802 of the insertion handle 800 along the insertion direction I. The insertion handle 800 can be configured (e.g., sized and shaped) such that the cannulation 816 aligns with a cannulation 426 of the intramedullary nail 400 when the insertion handle 800 is coupled to the intramedullary nail 400. The cannulation 816 can be configured (e.g., sized and shaped) so as to receive a rod, such as a guide rod or reaming rod, therethrough. The cannulation 816 can extend through the coupler 806. In some examples, the system 40 can comprise a fastener 500 that is configured as described above in relation to FIGS. 1 to 7 (or in another suitable manner) and that is configured to fasten the insertion handle 800 to the intramedullary nail 400 so as to positionally fix the insertion handle 800 and intramedullary nail 400 to one another.

The insertion handle 800 can include a gripping portion 810 that extends between the first transverse end 802 and the second transverse end 804 of the insertion handle 800. The gripping portion 810 can be between the coupler 806 and the coupler 808. The gripping portion 810 can include an outer surface 812 that extends between the first and second transverse ends 802 and 804. For example, the outer surface 812 can extend along the transverse direction T. The outer surface 812 can be sized and shaped to be gripped by a hand of a medical professional. Thus, the insertion handle 800 can be used to guide the intramedullary nail 400 along the guide rod or reaming rod into the medullary canal of the bone during insertion of the intramedullary nail 400, although it will be understood that the intramedullary nail 400 can be inserted without the guide rod or reaming rod.

The second transverse end 804 of the insertion handle 800 comprises a coupler 808 that is configured to couple the insertion handle 800 to the aiming guide 900. The coupler 808 includes at least one latch abutment surface 820 that is configured to be engaged by a latch 914 (shown in FIG. 18) of the aiming guide 900 so as to couple the insertion handle 800 and aiming guide 900 to one another at a first location. The coupler 808 further defines a recess 818 that is configured to receive the projection 916 (shown in FIG. 18) of the aiming guide 900 so as to couple the insertion handle 800 and aiming guide 900 to one another at a second location. The first and second locations can be offset from one another along the longitudinal direction L. For example, the first location can be offset from the second location along one of the insertion direction I and the rearward direction R. Thus, the latch abutment surface 820 can be offset from the recess 818 with respect to one of the insertion direction I and the rearward direction R. In some examples, the coupler 808 can define a second recess 818 that is configured to receive a second projection 916 (shown in FIG. 18) of the aiming guide 900 so as to couple the insertion handle 800 and aiming guide 900 to one another at a third location. The first location can be offset from the third location along another one of the insertion direction I and the rearward direction R. Thus, the latch abutment surface 820 can be offset from the second recess 818 with respect to another one of the insertion direction I and the rearward direction R.

The coupler 808 can have a coupler body 814 that extends from the gripping portion 810 along the insertion direction I. The coupler body 814 can have an inner end 814*a* and an outer end 814*b* that are offset from one another along the transverse direction T. The coupler body 814 can have opposed sides 814*c* that are offset from one another along a lateral direction A. The opposed sides 814*c* can extend between the inner and outer ends 814*a* and 814*b*. The latch abutment surface 820 can be defined between the leading end 805 and trailing end 803 of the insertion handle 800. The latch abutment surface 820 can be an internal surface that at least partially defines a locking recess 821 that extends into the outer end 814*b* of the coupler 808. The latch abutment surface 820 can face along the transverse direction T towards the first transverse end 802. The locking recess 821 can extend into the outer end 814*b* and turn towards the rearward direction R so that the latch abutment surface 820 extends generally along the rearward direction R. In alternative examples, the locking recess 821 can turn towards the insertion direction I. It will be understood that the latch abutment surface 820 can be alternatively defined.

The at least one recess 818 can extend into the outer end 814*b*. In some examples, the at least one recess 818 can include a pair of recesses 818 that are offset from one another along the insertion direction I. Each recess 818 can also be considered an alignment recess. When a projection 916 of the aiming guide 900 is received in a corresponding recess 818, the inner surface of the recess 818 can provide an interference with the projection 916 that prevents the projection 916 from translating along at least one of the insertion direction I and rearward direction R. It will be understood that, in alternative examples, each recess 818 can alternatively be implemented as a projection that receives a recess of the aiming guide 900. The outer end 814*b* of the coupler body 814 can define an outer surface that is configured to face a corresponding surface 918*a* (shown in FIG. 18) of the aiming guide 900 when the insertion handle 800 and aiming guide 900 are coupled to one another. In at least some examples, the outer surface of the coupler body 814 is configured to abut the corresponding surface 918*a* (shown in FIG. 18) of the aiming guide 900.

Figure 17:
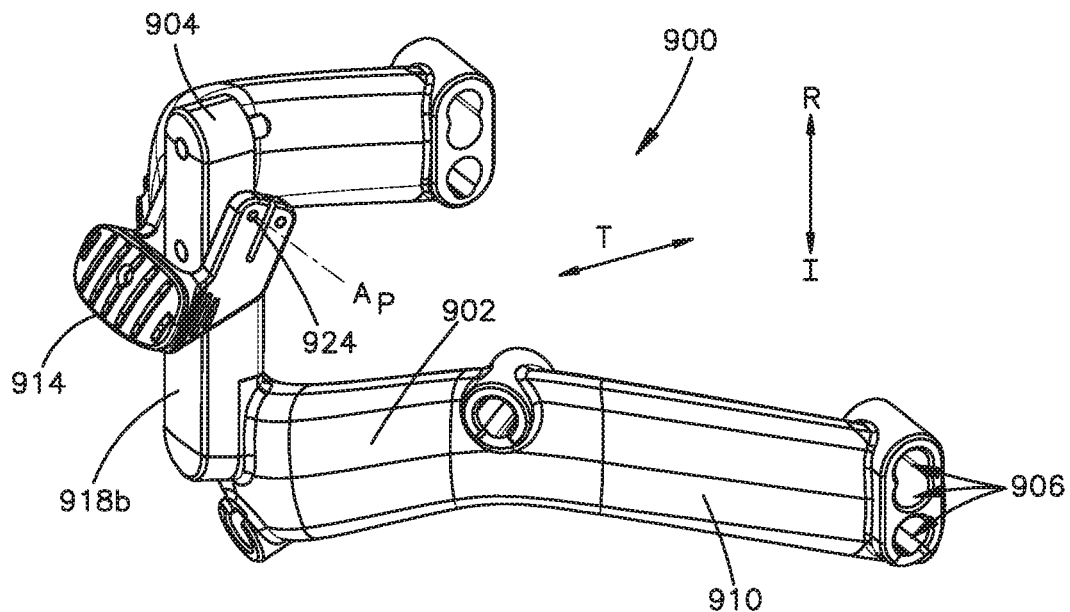
FIG. 17 shows a perspective view of an aiming guide of the intramedullary nail insertion system of FIG. 15.
Figure 18:
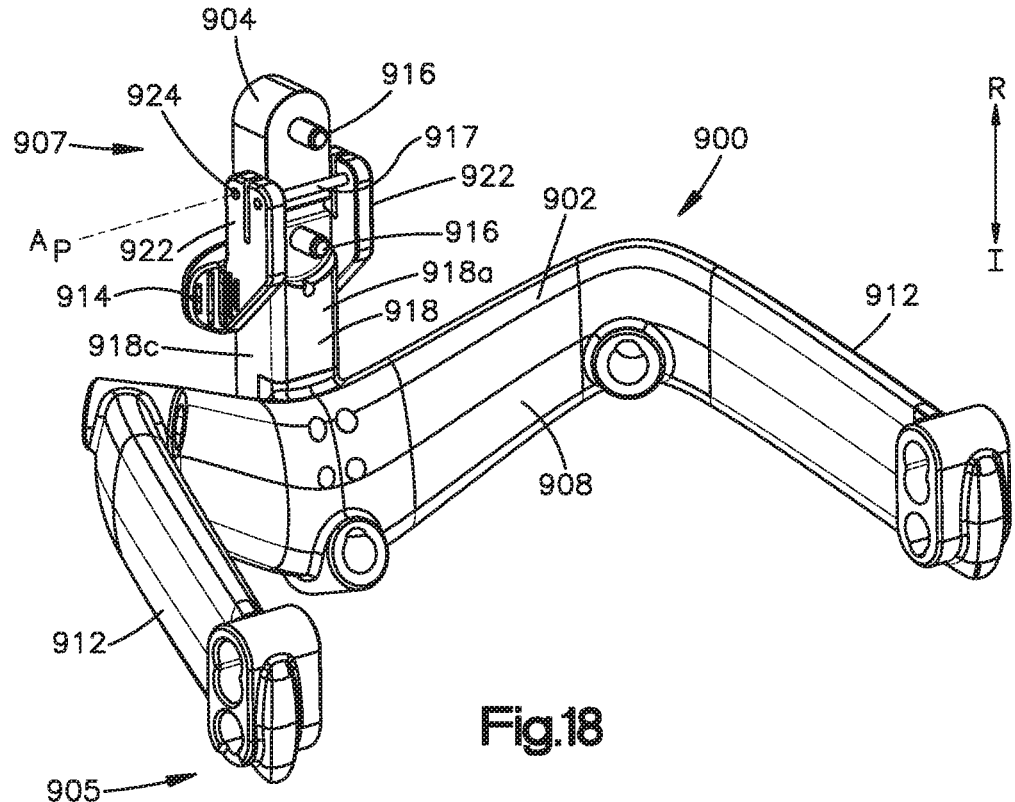
FIG. 18 shows another perspective view of the aiming guide of the intramedullary nail insertion system of FIG. 15.

With reference to FIGS. 17 and 18, the aiming guide 900 comprises a guide body 902 and a coupler 904. The guide body 902 defines at least one alignment aperture 906 therethrough. The coupler 904 is configured to couple the aiming guide 900 to the insertion handle 800 such that the at least one alignment aperture 906 is positioned to guide an instrument, such as a drill or reamer bit, towards at least one bone-anchor fixation hole 422 of the intramedullary nail 400 when the insertion handle 800 is coupled to the intramedullary nail 400.

The aiming guide 900 has an inner guide surface 908, and an outer guide surface 910 that is opposite the inner surface 908. The inner guide surface 908 can be positioned closer to the intramedullary nail 400 than the outer guide surface 910 when the aiming guide 900 is coupled to the intramedullary nail 400. The aiming guide 900 has a leading end 905 and a trailing end 907. The leading end 905 can be spaced from the trailing end 907 along the insertion direction I. Each alignment aperture 906 can extend entirely through the guide body 902 from the inner guide surface 908 to the outer guide surface 910. The guide body 902 can include at least one aiming arm 7912 that extends away from the coupler 904. For example, the guide body 902 can include a pair of aiming arms 912 that extend away from the coupler 904 in opposite directions. Each aiming arm 912 can extend partially around a central axis $A_L$ (shown in FIG. 15) that extends along the insertion direction I. For example, each aiming arm 912 can extend in a circumferential direction that extends circumferentially about the intramedullary nail 400 when the aiming guide 900 is coupled to the intramedullary nail 400. The aiming arms 912 can have any suitable configuration.

Each aiming arm 912 can include at least one alignment aperture 906. Each alignment aperture 906 can have a central axis $A_C$ that is aligned with one of the bone-anchor fixation holes 422 of the intramedullary nail 400 when the aiming guide 900 is coupled to the intramedullary nail 400 by the insertion handle 800. In some examples, at least one alignment aperture 906 can have an axis $A_C$ that is aligned with another one of the alignment apertures 906. For example, an alignment aperture 906 defined by a first one of the aiming arms 912 can have a central axis $A_C$ that is aligned with an alignment aperture 906 defined by a second one of the aiming arms 912.

The coupler 904 includes a latch 914 that is configured to engage the at least one latch abutment surface 820 of the insertion handle 800 so as to couple the insertion handle 800 and aiming guide 900 to one another at a first location. The coupler 904 further defines a projection 916 that is configured to be received in a recess 818 (shown in FIG. 16) of the insertion handle 800 so as to couple the insertion handle 800 and aiming guide 900 to one another at a second location. The projection 916 can extend from the coupler 904 along the transverse direction T. The first and second locations can be offset from one another along the longitudinal direction L. For example, the first location can be offset from the second location along one of the insertion direction I and rearward direction R. In some examples, the coupler 904 can define a second projection 916 that is configured to be received in a second recess 818 (shown in FIG. 16) of the insertion handle 800 so as to couple the insertion handle 800 and aiming guide 900 to one another at a third location. The second projection 916 can extend from the coupler 904 along the transverse direction T. The first location can be offset from the third location along another one of the insertion direction I and rearward direction R. It will be understood that, in alternative examples, one or both of the projections 916 can alternatively be implemented as a recess that receives a corresponding projection of the aiming guide 900.

The coupler 904 can have a coupler body 918 that extends along the insertion direction I. The coupler body 918 can have an inner end 918a and an outer end 918b that are offset from one another along the transverse direction T. The coupler body 918 can have opposed sides 918c that are offset from one another along a lateral direction A. Each aiming arm 912 can extend from one of the opposed sides 918c. The opposed sides 918c can extend between the inner and outer ends 918a and 918b.

The latch 914 can be configured to pivot about a pivot axis $A_P$. The pivot axis $A_P$ can extend along the lateral direction A. Thus, the latch 914 can be configured to pivot between a disengaged position (shown in FIG. 17), wherein the latch 914 is not positioned to engage a latch abutment surface 820 of the insertion handle 800, and an engaged position (shown in FIG. 18) wherein the latch 914 is positioned to engage a latch abutment surface 820 of the insertion handle 800. The latch 914 can include a spring that biases the latch 914 towards the engaged position, although the latch 914 can be devoid of the spring in other examples.

The latch 714 can include at least one engagement surface 917 that is configured to engage the latch abutment surface 820 of the insertion handle 800 when the latch 914 is in the engaged position. The at least one engagement surface 917 can be extend along the lateral direction A. In some examples, the at least one engagement surface 917 can be defined by a pin that extends along a central axis that extends along the lateral direction. The latch 914 can be configured to pivot between a disengaged configuration, wherein the at least one engagement surface 917 is not received in the locking recess 821 of the insertion handle 800, and an engaged position, wherein the at least one engagement surface 917 is received in the locking recess 821 of the insertion handle 800.

The latch 914 can include at least one arm 922 that is coupled to the coupler body 918. The coupler 904 can include a pivot pin 924 that couples the at least one arm 922 to the coupler body 918 such that the latch 914 pivots about the pivot pin 924. Thus, the at least one arm 922 can be pivotably coupled to the coupler body 918. In some examples, the latch 914 can include a pair of arms 922 that offset from one another along the lateral direction A. The pair of arms 922 can be coupled to opposing sides 918c of the coupler body 918. The pivot axis $A_P$ can extend from one of the arms 922 to the other one of the arms 922. In some examples, the at least one engagement surface 917 can extend between the pair of arms 922, such as from one of the arms 922 to the other one of the arms 922. However, it will be understood that, the latch 914 can be configured in another suitable manner in alternative examples.

The inner end 918a of the coupler body 918 can define an inner surface that is configured to face a corresponding outer surface of the insertion handle 800 when the insertion handle 800 and aiming guide 900 are coupled to one another. In at least some examples, the inner surface of the coupler body 918 is configured to abut the corresponding surface of the outer end 814b of the insertion handle 800. The at least one projection 916 can extend from the inner end 918a of the coupler body 918.

Figure 19:
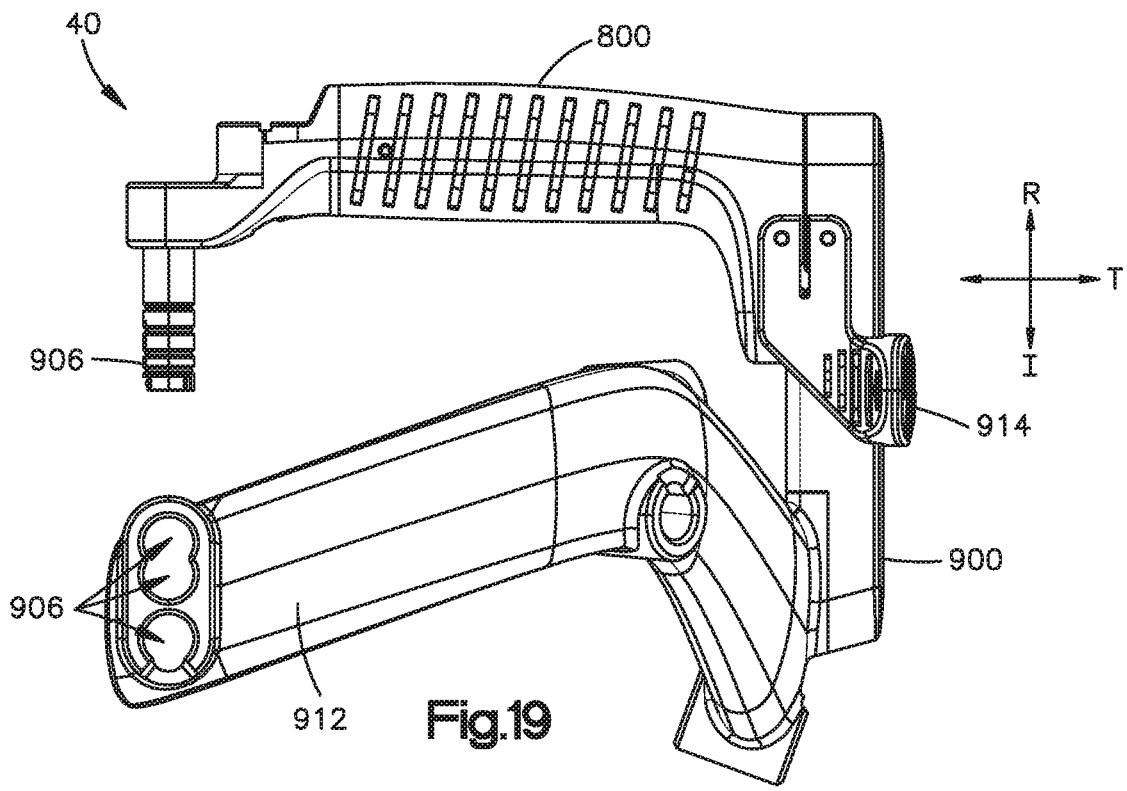
FIG. 19 shows a side view of the intramedullary nail insertion system of FIG. 15.
Figure 20:
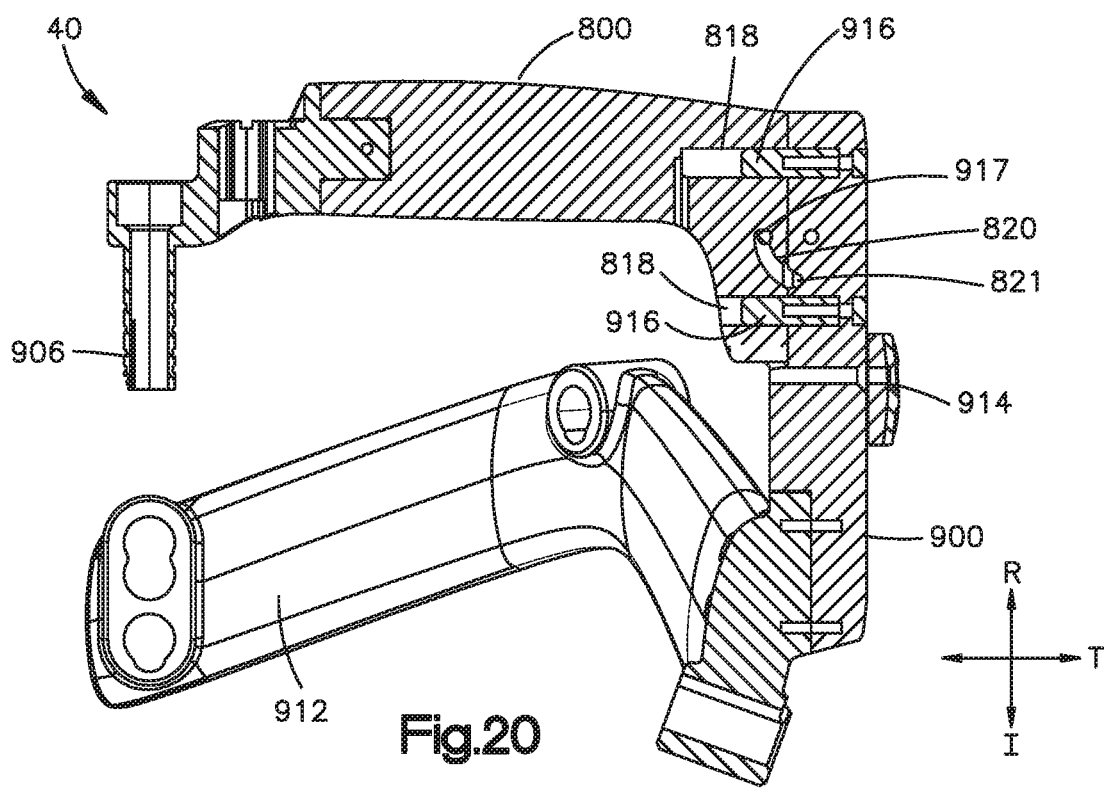
FIG. 20 shows a cross-sectional side view of the intramedullary nail insertion system of FIG. 15.

In operation, and with reference to FIGS. 19 and 20, the system 40 can be assembled by moving one of the insertion handle 800 and the aiming guide 900 towards one another along the transverse direction T so as to receive the at least one projection 916 of the aiming guide 900 into the recess 818 of the insertion handle 800. The at least one recess 818 is configured such that, when the at least one recess 818 receives the at least one projection 916, the insertion handle 800 limits translational movement of the projection 916 of the aiming guide 900 with respect to the insertion direction I and rearward direction R. As the at least one projection 916 is can be received the at least one recess 818, the inner end 918a of the coupler body 918 can abut the outer end 814b of the insertion handle 800.

The latch 914 can then be actuated so as to cause the latch 914 to engage the latch engagement surface 820 and thereby secure the aiming guide 900 and the insertion handle 800 to one another such that, when the insertion handle 800 is coupled to the intramedullary nail 400, at least one alignment aperture 906 of the aiming guide is positioned to guide an instrument towards at least one bone-anchor fixation hole 422 of the intramedullary nail 400. For example, the at least one latch 914 can be moved from the disengaged position to the engaged position such that the abutment surface 917 is received in the locking recess 821 and abuts the latch abutment surface 820. When the at least one latch 914 engages the at least one latch abutment surface 820, the insertion handle 800 can be fixed to the aiming guide 900 with respect to translation along the insertion direction I, translation along the transverse direction T, and rotation away from the aiming guide 900. The latch 914 can provide an audible and/or tactile feedback, such as click, when the latch 914 engages the at least one latch abutment surface 820.

To decouple the aiming guide 900 from the insertion handle 800, the user can move the latch 914 to move from the engaged position to the disengaged position. The user can then move one of the aiming guide 900 relative and the insertion handle 800 relative to the other along the transverse direction T so as to removes the at least one projection 916 from the at least one recess 818.

Figure 22:
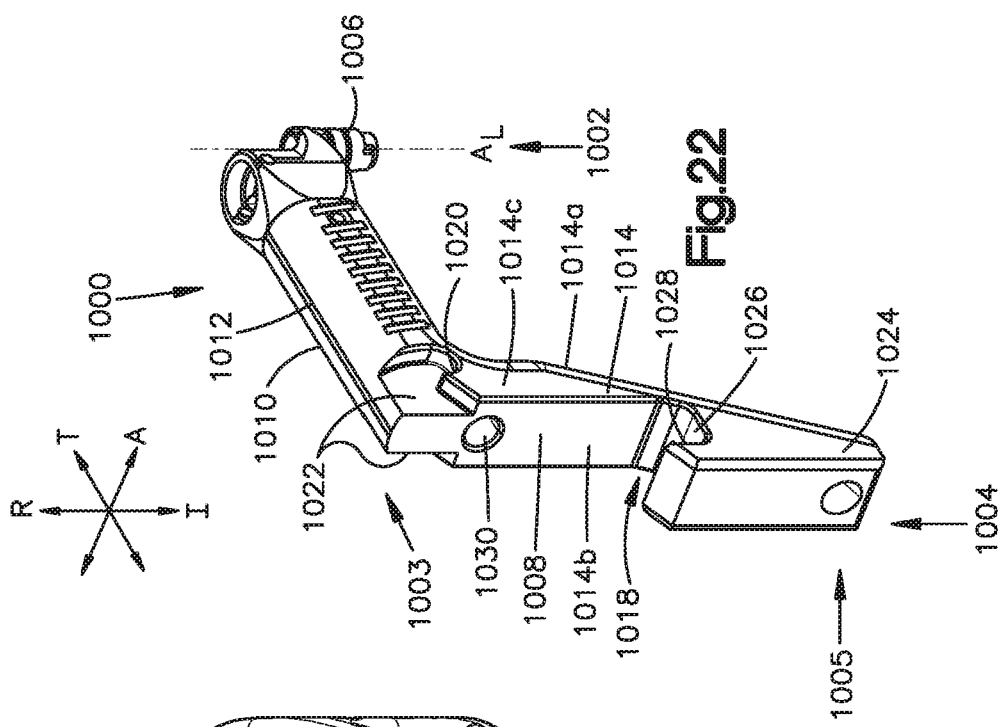
FIG. 22 shows a perspective view of an insertion handle of the intramedullary nail insertion system of FIG. 21.
Figure 21:
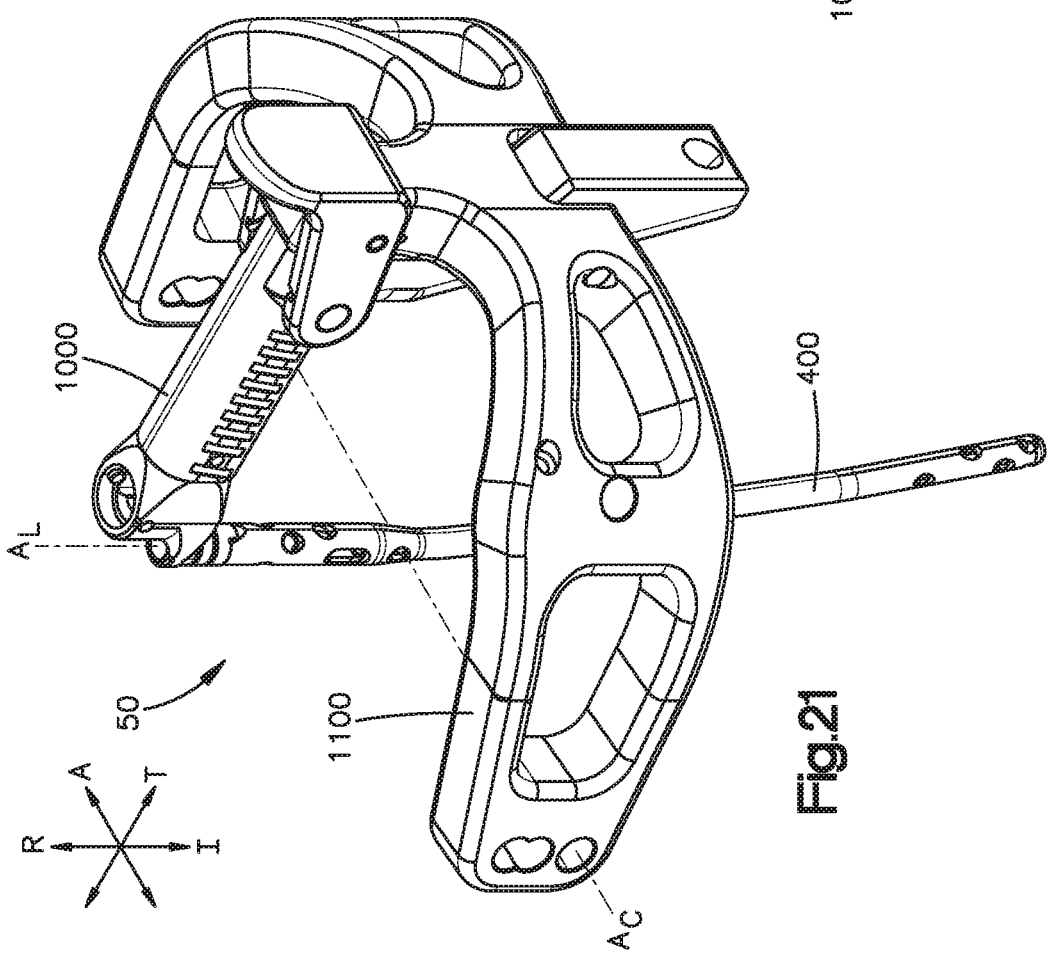
FIG. 21 shows a perspective view of an intramedullary nail insertion system according to even yet still another example.

Referring now to FIGS. 21 to 26, an example system 50 is shown having aiming guide 1100 with a coupler 1104 (FIG. 24) that defines a projection 1116 and a latch 1114, and an insertion handle 1000 with a coupler 1008 (FIG. 22) that defines a recess 1018 that receives the projection 1116 and a latch abutment surface 1020 that engages with the latch 1114. As shown in FIG. 22, the insertion handle 1000 has a first transverse end 1002 and a second transverse end 1004 that are offset from one another along a transverse direction T. The select transverse direction T can be a radial direction that extends radially out relative to an axis of the intramedullary nail 400 when the insertion handle 1000 is coupled to the intramedullary nail 400. The insertion handle 1000 can have a trailing end 1003, and a leading end 1005 that is offset from the trailing end 1003 along an insertion direction I.

The first transverse end 1002 of the insertion handle 1000 comprises a coupler 1006 that is configured to couple to the intramedullary nail 400. The coupler 1006 can be configured in a manner similar to that described above in relation to coupler 206 of FIGS. 1 to 7. Therefore, the description of coupler 206 above can equally apply to coupler 1006. The insertion handle 1000 can also define a cannulation 1016 that extends through the first transverse end 1002 of the insertion handle 1000 along the insertion direction I. The insertion handle 1000 can be configured (e.g., sized and shaped) such that the cannulation 1016 aligns with a cannulation 426 of the intramedullary nail 400 when the insertion handle 1000 is coupled to the intramedullary nail 400. The cannulation 1016 can be configured (e.g., sized and shaped) so as to receive a rod, such as a guide rod or reaming rod, therethrough. The cannulation 1016 can extend through the coupler 1006. In some examples, the system 50 can comprise a fastener 500 that is configured as described above in relation to FIGS. 1 to 7 (or in another suitable manner) and that is configured to fasten the insertion handle 1000 to the intramedullary nail 400 so as to positionally fix the insertion handle 1000 and intramedullary nail 400 to one another.

The insertion handle 1000 can include a gripping portion 1010 that extends between the first transverse end 1002 and the second transverse end 1004 of the insertion handle 1000. The gripping portion 1010 can be between the coupler 1006 and the coupler 1008. The gripping portion 1010 can include an outer surface 1012 that extends between the first and second transverse ends 1002 and 1004. For example, the outer surface 1012 can extend along the transverse direction T. The outer surface 1012 can be sized and shaped to be gripped by a hand of a medical professional. Thus, the insertion handle 1000 can be used to guide the intramedullary nail 400 along the guide rod or reaming rod into the medullary canal of the bone during insertion of the intramedullary nail 400, although it will be understood that the intramedullary nail 400 can be inserted without the guide rod or reaming rod.

The second transverse end 1004 of the insertion handle 1000 comprises a coupler 1008 that is configured to couple the insertion handle 1000 to the aiming guide 1100. The coupler 1008 includes at least one latch abutment surface 1020 that is configured to be engaged by a latch 1114 (shown in FIG. 24) of the aiming guide 1100 so as to couple the insertion handle 1000 and aiming guide 1100 to one another at a first location. In some examples, the at least one latch abutment surface 1020 can include a pair of opposed latch abutment surfaces 1020 that are offset from one another along the lateral direction A. The coupler 1008 further defines a recess 1018 that is configured to receive the projection 1116 (shown in FIG. 24) of the aiming guide 1100 so as to couple the insertion handle 1000 and aiming guide 1100 to one another at a second location. The first and second locations can be offset from one another along the longitudinal direction L. For example, the first location can be offset from the second location along the rearward direction R. Thus, the latch abutment surface 1020 can be offset from the recess 1018 with respect to the rearward direction R.

The coupler 1008 can have a coupler body 1014 that extends from the gripping portion 1010 along the insertion direction I. The coupler body 1014 can have an inner end 1014a and an outer end 1014b that are offset from one another along the transverse direction T. The coupler body 1014 can have opposed sides 1014c that are offset from one another along a lateral direction A. The opposed sides 1014c can extend between the inner and outer ends 1014a and 1014b. Each latch abutment surface 1020 can face towards the first transverse end 1002 of the insertion handle 1000. Each latch abutment surface 1020 can at least partially define a locking recess 1022 that is configured to receive an abutment surface 1120 of the latch 1114. Each locking recess 1022 can into the insertion handle along the insertion direction I such that the locking recess 1022 is open at the trailing end 1003. Additionally, or alternatively, each the locking recess 1022 can extend into the insertion handle along the transverse direction T towards the first transverse end 1002 such that the locking recess 1022 is open towards the second transverse end 1004. Additionally, or alternatively, each the locking recess 1022 can extend into the insertion handle 1000 along the lateral direction A such that the locking recess 1022 is open at a respective one of the sides of the insertion handle 1000.

The coupler 1008 can include a hook portion 1024 that can be configured in a manner similar to the hook portion 324 described above in regards to FIGS. 1 to 7. For example, the hook portion 1024 can extend from the coupler body 1014 along the transverse direction T. The hook portion 1024 can extend along the transverse direction T, away from the first transverse end 1002 of the insertion handle 1000. The recess 1018 can extend into the hook portion 1024 along the insertion direction I. The recess 1018 can terminate before the leading end 1005 of the insertion handle 1000. In one example, the recess 1018 can have a "U" shape, wherein the arms of the "U" shape are offset from one another along the transverse direction T. Thus, the recess 1018 can be defined by the outer end 1014b of the coupler body 1014, a bottom surface 1026 that extends away from the coupler body 1014, and an inner surface 1028 that extends from the bottom surface 1026 along the rearward direction R, the inner surface 1028 facing the outer end 1014b of the coupler body 1014. In some examples, the recess 1018 can extend entirely through the insertion handle 1000 along the lateral direction A. When the projection 1116 of the aiming guide 1100 is received in the recess 1018, the inner surface 1028 of the hook portion 1024 and the outer end 1014b of the coupler body 1014 can provide an interference with the projection 1116 that prevents the projection 1116 from translating along the transverse direction T with respect to the insertion handle 1000.

The outer end 1014b of the coupler body 1014 can define an outer surface that is configured to face a corresponding surface 1118 (shown in FIG. 24) of the aiming guide 1100 when the insertion handle 1000 and aiming guide 1100 are coupled to one another. In at least some examples, the outer surface of the coupler body 1014 is configured to abut the corresponding surface 1118 of the aiming guide 1100. The coupler 1008 can define at least one alignment recess 1030 that extends into the outer end 1014b of the coupler body 1014. Each alignment recess 1030 can be configured to receive a corresponding alignment pin 1132 (shown in FIG. 22) of the aiming guide 1100. It will be understood that, in alternative examples, the recess 1030 can alternatively be implemented as a pin that is received in a corresponding alignment recess of the aiming guide 1100.

Figure 23:
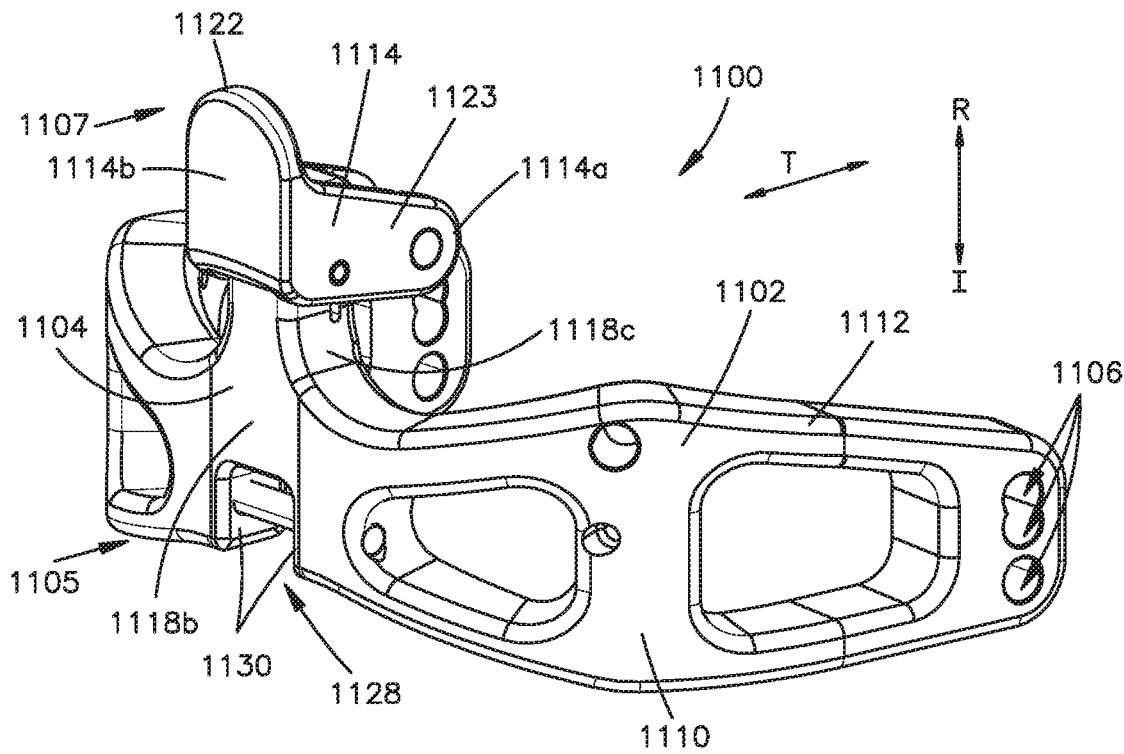
FIG. 23 shows a perspective view of an aiming guide of the intramedullary nail insertion system of FIG. 21.
Figure 24:
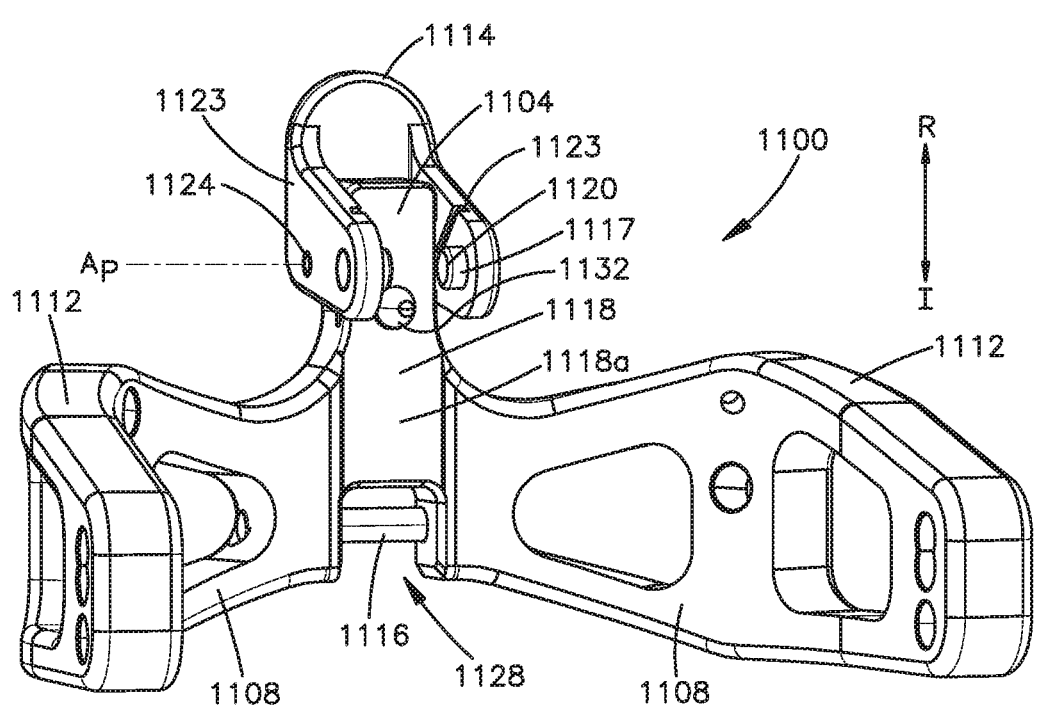
FIG. 24 shows another perspective view of the aiming guide of the intramedullary nail insertion system of FIG. 21.

With reference to FIGS. 23 and 24, the aiming guide 1100 comprises a guide body 1102 and a coupler 1104. The guide body 1102 defines at least one alignment aperture 1106 therethrough. The coupler 1104 is configured to couple the aiming guide 1100 to the insertion handle 1000 such that the at least one alignment aperture 1106 is positioned to guide an instrument, such as a drill or reamer bit, towards at least one bone-anchor fixation hole 422 of the intramedullary nail 400 when the insertion handle 1000 is coupled to the intramedullary nail 400.

The aiming guide 1100 has an inner guide surface 1108, and an outer guide surface 1110 that is opposite the inner surface 1108. The inner guide surface 1108 can be positioned closer to the intramedullary nail 400 than the outer guide surface 1110 when the aiming guide 1100 is coupled to the intramedullary nail 400. The aiming guide 1100 has a leading end 1105 and a trailing end 1107. The leading end 1105 can be spaced from the trailing end 1107 along the insertion direction I. Each alignment aperture 1106 can extend entirely through the guide body 1102 from the inner guide surface 1108 to the outer guide surface 1110. The guide body 1102 can include at least one aiming arm 1112 that extends away from the coupler 1104. For example, the guide body 1102 can include a pair of aiming arms 1112 that extend away from the coupler 1104 in opposite directions. Each aiming arm 1112 can extend partially around a central axis $A_L$ that extends along the insertion direction I. For example, each aiming arm 1112 can extend in a circumferential direction that extends circumferentially about the intramedullary nail 400 when the aiming guide 1100 is coupled to the intramedullary nail 400. The aiming arms 1112 can have any suitable configuration.

Each aiming arm 1112 can include at least one alignment aperture 1106. Each alignment aperture 1106 can have a central axis $A_C$ that is aligned with one of the bone-anchor fixation holes 422 of the intramedullary nail 400 when the aiming guide 1100 is coupled to the intramedullary nail 400 by the insertion handle 1000. In some examples, at least one alignment aperture 1106 can have an axis $A_C$ that is aligned with another one of the alignment apertures 1106. For example, an alignment aperture 1106 defined by a first one of the aiming arms 1112 can have a central axis $A_C$ that is aligned with an alignment aperture 1106 defined by a second one of the aiming arms 1112.

The coupler 1104 includes a latch 1114 that is configured to engage the at least one latch abutment surface 1020 of the insertion handle 1000 so as to couple the insertion handle 1000 and aiming guide 1100 to one another at a first location. The coupler 1104 further defines a projection 1116 that is configured to be received in the recess 1018 of the insertion handle 1000 so as to couple the insertion handle 1000 and aiming guide 1100 to one another at a second location. The first and second locations can be offset from one another along the longitudinal direction L. For example, the second location can be offset from the first location along the insertion direction I. Thus, the projection 1116 can be offset from the latch 1114 with respect to the insertion direction I. It will be understood, however, that the locations of the projection 1116 and the latch 1114 can be reversed in alternative examples such that the latch 1114 is offset from the projection 1116 with respect to the insertion direction I.

The coupler 1104 can have a coupler body 1118 that extends along the insertion direction I. The coupler body 1118 can have an inner end 1118a and an outer end 1118b that are offset from one another along the transverse direction T. The coupler body 1118 can have opposed sides 1118c that are offset from one another along a lateral direction A. Each aiming arm 1112 can extend from one of the opposed sides 1118c. The opposed sides 1118c can extend between the inner and outer ends 1118a and 1118b.

The latch 1114 can be configured to pivot about a pivot axis $A_P$. The pivot axis $A_P$ can extend along the lateral direction A. Thus, the latch 1114 can be configured to pivot between a disengaged position, wherein the latch 1114 does not engage a latch abutment surface 1020 of the insertion handle 1000, and an engaged position wherein the latch 1114 engages a latch abutment surface 1020 of the insertion handle 1000. The latch 1114 can include a spring 1115 that biases the latch 1114 towards the engaged position, although examples of the disclosure are not so limited.

The latch 1114 can include at least one engagement surface 1117 that is configured to engage the latch abutment surface 1020 of the insertion handle 1000 when the latch 1114 is in the engaged position. The latch 1114 can include at least one protrusion 1120 that defines the at least one engagement surface 1117. For example, the latch 1114 can include a pair of engagement surfaces 1117, each configured to engage a respective latch abutment surface 1020 of the insertion handle 1000. The pair of engagement surfaces 1117 can be offset from one another along the lateral direction A.

The latch 1114 can include a first latch end 1114a and a second latch end 1114b that are offset from one another along the transverse direction T. The first latch end 1114a can include the at least one engagement surface 1117. The second latch end 1114b can include an actuation member 1122 that is configured to be depressed and released by a user, such as a medical professional, so as to move the latch 1114 between the engaged position and the disengaged position. For example, the latch 1114 can be configured such that, when the actuation member 1122 is depressed, the at least one engagement surface 1117 moves to a disengaged configuration, and when the actuation member 1122 is released or lifted, the at least one engagement surface 117 moves to the engaged position.

The latch 1114 can include at least one arm 1123 that is coupled to the coupler body 1118. The coupler 1104 can include a pivot pin 1124 that couples the at least one arm 1123 to the coupler body 1118 such that the latch 1114 pivots about the pivot pin 1124. Thus, the at least one arm 1123 can be pivotably coupled to the coupler body 1118. In some examples, the latch 1114 can include a pair of arms 1123 that offset from one another along the lateral direction A. The pair of arms 1123 can be coupled to opposing sides 1118c of the coupler body 1118. Each engagement surface 1117 can extend from one of the arms 1123. For example, each engagement surface 1117 can extend inwardly from one of the arms 1123. The pivot axis $A_P$ can extend from one of the arms 1123 to the other one of the arms 1123. However, it will be understood that, the latch 1114 can be configured in another suitable manner in alternative examples.

The projection 1116 can include an outer surface that extends along the lateral direction A. The projection 1116 can be a pin that has a central axis that extends along the lateral direction A. The aiming guide 1100 can define a recess 1128 that into the leading end 1105 towards the trailing end 1107. In one example, the recess 1128 can have a "U" shape. The recess 1128 can entirely extend through the aiming guide 1100 from the inner surface 1108 to the outer surface 1110. The aiming guide 1100 can including opposing inner surfaces 1130 that are offset from one another along the lateral direction A and that define the recess 1128. The projection 1116 can be disposed within the recess 1128. For example, the projection 1116 can extend from one of the inner surfaces 1130 to the other one of the inner surfaces 1130. In alternative examples, the projection 1116 can be configured in another suitable manner. For example, the aiming guide 1100 can devoid of the recess 1128, and the projection 1116 can instead extend from the leading end 1105 of the aiming guide 1100 along the insertion direction I.

The inner end 1118a of the coupler body 1118 can define an inner surface that is configured to face a corresponding outer surface of the insertion handle 1000 when the insertion handle 1000 and aiming guide 1100 are coupled to one another. In at least some examples, the inner surface of the coupler body 1118 is configured to abut the corresponding surface of the outer end 1014b of the insertion handle 1000. The coupler 1104 can define at least one alignment pin 332 that extends from the inner end 1118a of the coupler body 1118. Each alignment pin 332 can be configured to be received a corresponding alignment recess 1030 of the insertion handle 1000. It will be understood that, in alternative examples, each alignment pin 332 can alternatively be implemented as an alignment recess that receives a corresponding alignment pin of the insertion handle 1000.

Figure 25:
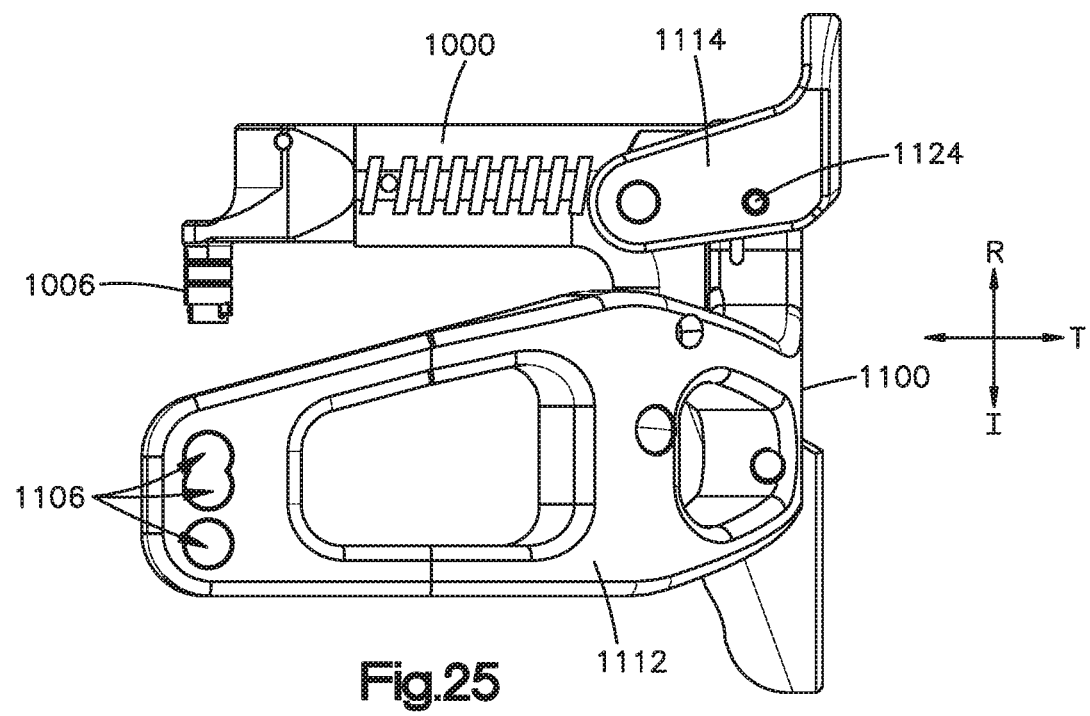
FIG. 25 shows a side view of the intramedullary nail insertion system of FIG. 21.
Figure 26:
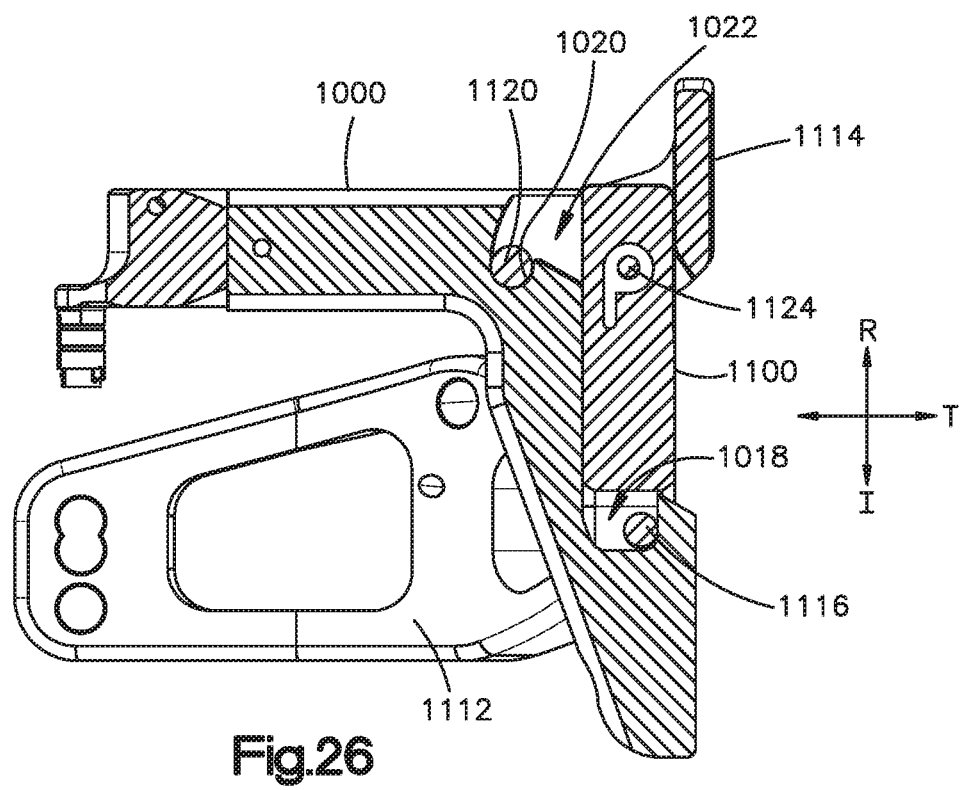
FIG. 26 shows a cross-sectional side view of the intramedullary nail insertion system of FIG. 21.

In operation, and with reference to FIGS. 25 and 26, the system 50 can be assembled by moving the aiming guide 1100 towards the insertion handle 1000 along the insertion direction I so as to receive the projection 1116 of the aiming guide 1100 into the recess 1018 of the insertion handle 1000. The recess 1018 is configured such that, when the recess 1018 receives the projection 1116, the insertion handle 1000 limits translational movement of the aiming guide 1100 with respect to the insertion direction I. However, the aiming guide 1100 can be pivoted or rotated relative to the insertion handle 1000 about the projection 1116 such that the trailing end 1107 of the aiming guide 1100 moves towards the insertion handle 1000. As the aiming guide 1100 is pivoted, each alignment pin 332 can be received in a corresponding one of the alignment recesses 1030. Additionally, or alternatively, the inner end 1118a of the coupler body 1118 can abut the outer end 1014b of the insertion handle 1000.

The latch 1114 can then be actuated so as to cause the latch 1114 to engage the latch engagement surface 1020 and thereby secure the aiming guide 1100 and the insertion handle 1000 to one another such that, when the insertion handle 1000 is coupled to the intramedullary nail 400, at least one alignment aperture 1106 of the aiming guide is positioned to guide an instrument towards at least one bone-anchor fixation hole 422 of the intramedullary nail 400. For example, the at least one latch 1114 can be moved from the disengaged position to the engaged position such that the abutment surface 1117 abuts the latch abutment surface 1020. When the at least one latch 1114 engages the at least one latch abutment surface 1020, the insertion handle 1000 can be fixed to the aiming guide 1100 with respect to translation along the insertion direction I, translation along the transverse direction T, and rotation away from the aiming guide 1100. The latch 1114 can provide an audible and/or tactile feedback, such as click, when the latch 1114 engages the at least one latch abutment surface 1020.

To decouple the aiming guide 1100 from the insertion handle 1000, the user can move the latch 1114 from the engaged position to the disengaged position. The user can then pivot the aiming guide 1100 relative to the insertion handle 1000 about the projection 1116 so that the trailing end 1107 of the aiming guide 1100 moves away from the insertion handle 1000, and the user can remove the projection 1116 of the aiming guide 1100 from the recess 1018 of the insertion handle 1000 along the rearward direction R.

It will be understood that, in alternative examples, the insertion handle can include the latch that engages the aiming guide.

It will be understood that the insertion handle can alternatively be referred to as a spacer that is configured to couple the aiming guide to the intramedullary nail so as to space the aiming guide from the intramedullary nail.

In one example, a system, comprises an insertion handle and an aiming arm. The insertion handle is configured to couple to an intramedullary nail. The insertion handle includes a coupler that defines one of a recess and a projection, and one of a latch and a latch abutment surface. The aiming guide includes a guide body that defines at least one alignment aperture therethrough. The aiming guide includes another coupler configured to couple the guide body to the coupler of the insertion handle such that the at least one alignment aperture is positioned to guide an instrument towards at least one bone-anchor fixation hole of the intramedullary nail when the insertion handle is coupled to the intramedullary nail. The other coupler defines another of the recess and the projection, and another of the latch and the abutment surface. The coupler and the other coupler are configured to be coupled to one another by receiving the projection in the recess and by engaging the latch with the abutment surface.

In another example, an intramedullary nail insertion handle comprises a first end and a second end that are offset from one another along a transverse direction. The nail comprises a first coupler configured to couple the insertion handle to an intramedullary nail, and a second coupler that is offset from the first coupler along the transverse direction. The second coupler is configured to couple the insertion handle to an aiming arm. The second coupler defines one of a recess and a projection that is configured to engage another one of a recess and a projection of the aiming arm, and one of a latch and a latch abutment surface that is configured to engage another one of a latch and abutment surface of the aiming arm.

In yet another example, an aiming guide, comprises a guide body and a coupler. The guide body defines at least one alignment aperture therethrough. The coupler is configured to couple the guide body to an insertion handle such that the at least one alignment aperture is positioned to guide an instrument towards at least one bone-anchor fixation hole of the intramedullary nail when the insertion handle is coupled to the intramedullary nail. The coupler defines one of a recess and a projection that is configured to engage another one of a recess and a projection of the aiming arm, and one of a latch and a latch abutment surface that is configured to engage another one of a latch and abutment surface of the aiming arm.

It will be understood that reference herein to "a" or "one" to describe a feature such as a component or step does not foreclose additional features or multiples of the feature. For instance, reference to a device having or defining "one" of a feature does not preclude the device from having or defining more than one of the feature, as long as the device has or defines at least one of the feature. Similarly, reference herein to "one of" a plurality of features does not foreclose the invention from including two or more of the features. For instance, reference to a device having or defining "one of a protrusion and a recess" does not foreclose the device from having both a protrusion and a recess, or from having more than one protrusion or more than one recess.

It should be noted that the illustrations and descriptions of the examples shown in the figures are for exemplary purposes only, and should not be construed limiting the disclosure. One skilled in the art will appreciate that the present disclosure contemplates various examples. Additionally, it should be understood that the concepts described above with the above-described examples may be employed alone or in combination with any of the other examples described above. It should further be appreciated that the various alternative examples described above with respect to one illustrated example can apply to all examples as described herein, unless otherwise indicated.

Unless explicitly stated otherwise, each numerical value and range should be interpreted as being approximate as if the word "about," "approximately," or "substantially" preceded the value or range. The terms "about," "approximately," and "substantially" can be understood as describing a range that is within 15 percent of a specified value unless otherwise stated.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements, and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous and are used inclusively, in an open-ended fashion, and do not exclude additional elements, features, acts, operations, and so forth.

While certain examples have been described, these examples have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various examples of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The words "inward," "outward," "upper," "lower," "distal," and "proximal," refer to directions toward or away from, respectively, the geometric center of the intramedullary nail.

What is claimed:

1. A system, comprising:
an insertion handle configured to couple to an intramedullary nail, the insertion handle including a first coupler that defines one of a recess and a corresponding projection, and one of a latch and a corresponding latch abutment surface; and
an aiming guide that includes a guide body that defines at least one alignment aperture therethrough, the aiming guide including a second coupler configured to couple the guide body to the first coupler of the insertion handle such that the at least one alignment aperture is positioned to guide an instrument towards at least one bone-anchor fixation hole of the intramedullary nail when the insertion handle is coupled to the intramedullary nail, the second coupler defining another of the recess and the corresponding projection, and another of the latch and the corresponding latch abutment surface,
wherein the first and second couplers are configured to be coupled to one another by receiving the corresponding projection in the recess and engaging the latch with the corresponding latch abutment surface,
wherein the latch includes at least one arm that is pivotably coupled to a body of a respective one of the first and second couplers,
wherein the at least one arm includes a pair of arms and the latch includes an engagement surface that extends between the pair of arms, the engagement surface configured to engage the corresponding latch abutment surface.

2. The system of claim 1, wherein:
the insertion handle is configured to couple to the intramedullary nail such that the intramedullary nail extends along a longitudinal direction;
the latch is configured to engage the latch abutment surface at a first location; and
the recess is configured to receive the corresponding projection at a second location, offset from the first location along the longitudinal direction.

3. The system of claim 1, comprising a pivot pin that couples the latch to a body of a respective one of the first and second couplers such that the latch pivots about the pivot pin.

4. The system of claim 1, wherein the first and second couplers are configured to be coupled to one another by first receiving the projection in the recess and then rotating the insertion handle and aiming guide relative to one another and engaging the latch with the corresponding latch abutment surface.

5. The system of claim 1, wherein the latch includes a pin that defines the engagement surface, the pin extending along a central axis that extends from one of the arms to the other one of the arms, and the corresponding latch abutment surface at least partially defines a locking recess that is configured receive the pin.

6. The system of claim 1, wherein the at least one arm defines a hook that is configured to engage the corresponding latch abutment surface.

7. The system of claim 1, wherein the first coupler defines the recess and second coupler defines the corresponding projection.

8. The system of claim 1, wherein the first coupler defines the corresponding latch abutment surface and second coupler defines the latch.

9. The system of claim 1, wherein:
the insertion handle is configured to couple to the intramedullary nail such that the intramedullary nail extends along a longitudinal direction;
the aiming guide is configured to be supported by the insertion handle so as to be offset from the intramedullary nail along a transverse direction; and the latch is configured to pivot about an axis that extends along a direction that is angularly offset from both the longitudinal direction and the transverse direction.

10. A system, comprising:
an insertion handle configured to couple to an intramedullary nail such that the intramedullary nail extends along a longitudinal direction;
an aiming guide that includes a guide body that defines at least one alignment aperture therethrough, the aiming guide configured to be supported by the insertion handle such that, when the insertion handle is coupled to the intramedullary nail, the aiming guide is offset from the intramedullary nail along a transverse direction and the at least one alignment aperture is positioned to guide an instrument towards at least one bone-anchor fixation hole of the intramedullary nail; and
a latch pivotally coupled to a body of one of the insertion handle and the aiming guide, the latch configured to pivot about a pivot axis that extends along a lateral direction so as to move between a disengaged position, wherein the latch does not secure the insertion handle and the aiming guide to one another, and an engaged position, wherein the latch engages a corresponding latch abutment surface of the other one of the insertion handle and the aiming guide so as to secure the insertion handle and the aiming guide to one another,
wherein the latch includes at least one arm that is pivotably coupled to a body of a respective one of the first and second couplers,
wherein the at least one arm includes a pair of arms and the latch includes an engagement surface that extends between the pair of arms, the engagement surface configured to engage the corresponding latch abutment surface.

11. The system of claim 10, wherein the lateral direction is angularly offset from the longitudinal direction and the transverse direction.

12. The system of claim 10, comprising a pivot pin that couples the latch to the body of the one of the first and second couplers such that the latch pivots about the pivot pin.

* * * * *